(12) United States Patent
Lauks

(10) Patent No.: US 8,007,648 B2
(45) Date of Patent: Aug. 30, 2011

(54) INTEGRATED ELECTROKINETIC DEVICES AND METHODS OF MANUFACTURE

(76) Inventor: Imants R. Lauks, Ottawa (CA)

( * ) Notice: Subject to any disclaimer, the term of this patent is extended or adjusted under 35 U.S.C. 154(b) by 1160 days.

(21) Appl. No.: 11/697,116

(22) Filed: Apr. 5, 2007

(65) Prior Publication Data
US 2007/0170062 A1    Jul. 26, 2007

Related U.S. Application Data

(62) Division of application No. 09/871,821, filed on Jun. 4, 2001, now Pat. No. 7,214,300.

(51) Int. Cl.
*G01D 7/06* (2006.01)
(52) U.S. Cl. .......... 204/600; 204/450; 422/504
(58) Field of Classification Search .......... 204/450, 204/600; 422/100, 504, 505
See application file for complete search history.

(56) References Cited

U.S. PATENT DOCUMENTS

| | | | |
|---|---|---|---|
| 4,048,377 A | 9/1977 | Boschetti et al. | |
| 4,551,209 A | 11/1985 | Lauks | |
| 4,574,040 A | 3/1986 | Delony et al. | |
| 4,613,422 A | 9/1986 | Lauks | |
| 4,628,035 A | 12/1986 | Tokinaga et al. | |
| 4,629,424 A | 12/1986 | Lauks et al. | |
| 4,663,015 A | 5/1987 | Sleeter et al. | |
| 4,668,359 A | 5/1987 | Postle et al. | |
| 4,739,380 A | 4/1988 | Lauks et al. | |
| 4,746,551 A * | 5/1988 | Allen et al. ............. | 204/456 |
| 4,864,229 A | 9/1989 | Lauks et al. | |
| 4,908,112 A | 3/1990 | Pace | |
| 4,933,048 A | 6/1990 | Lauks | |
| 4,954,087 A | 9/1990 | Lauks et al. | |
| 4,997,537 A | 3/1991 | Karger et al. | |
| 4,999,340 A | 3/1991 | Hoffman et al. | |
| 5,008,616 A | 4/1991 | Lauks et al. | |
| 5,009,766 A | 4/1991 | Lauks | |
| 5,055,415 A | 10/1991 | Imai et al. | |
| 5,063,081 A | 11/1991 | Cozzette et al. | |

(Continued)

FOREIGN PATENT DOCUMENTS

DE    10011022    9/2001

(Continued)

OTHER PUBLICATIONS

Fodor et al., "Light-Directed, Spatially Addressable Parallel Chemical Synthesis", Research Article, Science, vol. 251, pp. 767-773, Feb. 15, 1991.

(Continued)

*Primary Examiner* — Kaj K Olsen
(74) *Attorney, Agent, or Firm* — Borden Ladner Gervais LLP

(57) ABSTRACT

Devices with electrokinetic elements are disclosed as well as their method of microfabrication for use in micro-scale analysis, mixture separation and reaction. The devices consist of solid hydrophilic-matrix films that have been microfabricated into a variety of micro-scale structures. These structures include hydrophilic-matrix conductors for electrokinetic species transport and separation. They also include hydrophilic-matrix cladding containing chemical species adjacent to either an open conduit or a hydrophilic matrix conductor. Also described are other integrated microstructures consisting of hydrophilic-matrix materials such as micro-reaction zones for retaining chemical species for on-chip chemical reactions and integrated detection structures for on-chip species detection. In general, a hydrophilic matrix on a substrate functions as a conductor that is covered by an electrically insulating, preferably water permeable material.

17 Claims, 10 Drawing Sheets

U.S. PATENT DOCUMENTS

| | | | |
|---|---|---|---|
| 5,089,111 A | 2/1992 | Zhu et al. | |
| 5,096,669 A | 3/1992 | Lauks et al. | |
| 5,112,455 A | 5/1992 | Cozzette et al. | |
| 5,124,661 A | 6/1992 | Zelin et al. | |
| 5,126,022 A | 6/1992 | Soane et al. | |
| 5,141,612 A | 8/1992 | Schomburg et al. | |
| 5,167,783 A | 12/1992 | Holloway | |
| D332,833 S | 1/1993 | Lauks et al. | |
| 5,180,480 A | 1/1993 | Manz | |
| 5,192,412 A | 3/1993 | Kambara et al. | |
| 5,194,133 A | 3/1993 | Clark et al. | |
| 5,200,051 A | 4/1993 | Cozzette et al. | |
| 5,207,886 A | 5/1993 | Lauer et al. | |
| 5,212,050 A | 5/1993 | Mier et al. | |
| 5,223,117 A * | 6/1993 | Wrighton et al. | 204/415 |
| D337,164 S | 7/1993 | Lauks et al. | |
| 5,296,114 A | 3/1994 | Manz | |
| 5,300,779 A | 4/1994 | Hillman et al. | |
| 5,304,487 A | 4/1994 | Wilding et al. | |
| 5,397,451 A | 3/1995 | Senda et al. | |
| 5,416,026 A | 5/1995 | Davis | |
| 5,429,734 A | 7/1995 | Gajar et al. | |
| 5,439,578 A | 8/1995 | Dovichi et al. | |
| 5,447,440 A | 9/1995 | Davis et al. | |
| 5,466,575 A | 11/1995 | Cozzette et al. | |
| 5,514,253 A | 5/1996 | Davis et al. | |
| 5,543,023 A | 8/1996 | Lugojan | |
| 5,554,339 A | 9/1996 | Cozzette et al. | |
| 5,585,069 A | 12/1996 | Zanzucchi et al. | |
| 5,593,638 A | 1/1997 | Davis | |
| 5,599,432 A | 2/1997 | Manz et al. | |
| 5,605,664 A | 2/1997 | Lauks et al. | |
| 5,609,824 A | 3/1997 | Lauks et al. | |
| 5,614,416 A | 3/1997 | Lauks et al. | |
| 5,627,022 A | 5/1997 | Renfrew et al. | |
| 5,628,890 A | 5/1997 | Carter et al. | |
| 5,628,961 A | 5/1997 | Davis et al. | |
| 5,632,957 A | 5/1997 | Heller et al. | |
| 5,637,469 A | 6/1997 | Wilding et al. | |
| 5,638,828 A | 6/1997 | Lauks et al. | |
| 5,653,243 A | 8/1997 | Lauks et al. | |
| 5,661,028 A | 8/1997 | Foote | |
| 5,666,967 A | 9/1997 | Lauks et al. | |
| 5,746,901 A | 5/1998 | Balch et al. | |
| 5,750,015 A | 5/1998 | Soane et al. | |
| 5,770,029 A | 6/1998 | Nelson et al. | |
| 5,779,650 A | 7/1998 | Lauks et al. | |
| 5,789,253 A | 8/1998 | Lauks et al. | |
| 5,800,690 A | 9/1998 | Chow et al. | |
| 5,821,399 A | 10/1998 | Zelin | |
| 5,837,446 A | 11/1998 | Cozzette et al. | |
| 5,837,454 A | 11/1998 | Cozzette et al. | |
| 5,858,195 A | 1/1999 | Ramsey | |
| 5,906,723 A | 5/1999 | Mathies et al. | |
| 5,954,931 A | 9/1999 | Maracas et al. | |
| 6,004,442 A | 12/1999 | Choulga et al. | |
| 6,010,463 A | 1/2000 | Lauks et al. | |
| 6,010,608 A | 1/2000 | Ramsey | |
| 6,013,166 A | 1/2000 | Heller | |
| 6,017,696 A | 1/2000 | Heller | |
| 6,030,827 A | 2/2000 | Davis et al. | |
| 6,093,296 A | 7/2000 | Soane et al. | |
| 6,103,199 A | 8/2000 | Bjornson et al. | |
| 6,129,828 A | 10/2000 | Sheldon, III et al. | |
| 6,306,594 B1 | 10/2001 | Cozzette et al. | |
| 6,379,883 B2 | 4/2002 | Davis et al. | |
| 6,438,498 B1 | 8/2002 | Opalsky et al. | |
| 6,451,191 B1 | 9/2002 | Bentsen et al. | |
| 6,488,828 B1 | 12/2002 | Bhullar et al. | |
| 6,750,053 B1 | 6/2004 | Wildrig Opalsky et al. | |
| 7,074,610 B2 | 7/2006 | Cozzette et al. | |
| 2002/0177238 A1 | 11/2002 | Karp et al. | |
| 2002/0177958 A1 | 11/2002 | Widrig Opalsky et al. | |
| 2003/0170881 A1 | 9/2003 | Davis et al. | |
| 2004/0018577 A1 | 1/2004 | Emerson Campbell et al. | |
| 2004/0175296 A1 | 9/2004 | Opalsky et al. | |
| 2005/0054078 A1 | 3/2005 | Miller et al. | |
| 2006/0046275 A1 | 3/2006 | Collier et al. | |
| 2006/0160164 A1 | 7/2006 | Miller et al. | |
| 2007/0015977 A1 | 1/2007 | McCann et al. | |

FOREIGN PATENT DOCUMENTS

| | | |
|---|---|---|
| EP | 1063204 | 12/2000 |
| EP | 1174716 | 1/2002 |
| EP | 1063204 A3 | 8/2002 |
| GB | 2216258 | 10/1989 |
| JP | H11- 30605 A1 | 6/1998 |
| WO | 00/43766 | 7/2000 |

OTHER PUBLICATIONS

Harrison et al., "Capillary Electrophoresis and Sample Injection Systems Integrated on a Planar Glas Chip", Anal. Chem. vol. 64, No. 17, pp. 1926-1932, Sep. 1, 1992.

Harrison et al., "Micromachining a Minaturized Capillary Electrophoresis-Based Chemical Analysis System on a Chip", Science, vol. 261, pp. 895-897, Aug. 13, 1993.

Harmon et al., "Mathematical Treatment of Electrophoretically Mediated Microanalysis", Anal. Chem., vol. 65, No. 19, pp. 2655-2662, Oct. 1, 1993.

Fan e al., "Micromachining of Capillary Electrophoresis Injectors and Separators on Glass Chips and Evaluation of Flow at Capillary Intersections", Anal. Chem., vol. 66, No. 1, pp. 177-184, Jan. 1, 1994.

Jacobson et al., "Effects of Injection schemes and Column Geometry on the Performance of Microchip Electrophoresis Devices", Anal. Chem., vo. 66, No. 7, pp. 1107-1113, Apr. 1, 1994.

Jacobson et al., "High-Speed Separations on a Microchip", Anal. Chem., vol. 66, No. 7, pp. 1114-1118, Apr. 1, 1994.

Dasgupta et al., "Electroosmosis: A reliable Fluid Propulsion System for Flow Inection Analysis", Anal. Chem., vol. 66, No. 11, Jun. 1, 1994, pp. 1792-1798.

Harmon et al., "Selectivity in Electrophoretically Mediated Microanalysis by Control of Product Detection Time", Anal. Chem., vol. 66, No. 21, pp. 3797-3805, 1994.

Woolley et al., "Ultra-High-Speed DNA Fragment Separations using Microfabricated Capillary Array Electrophoresis Chips", Proc. Natl. Acad. Sci. USA, vol. 91, pp. 11348-11352, Nov. 1994.

* cited by examiner

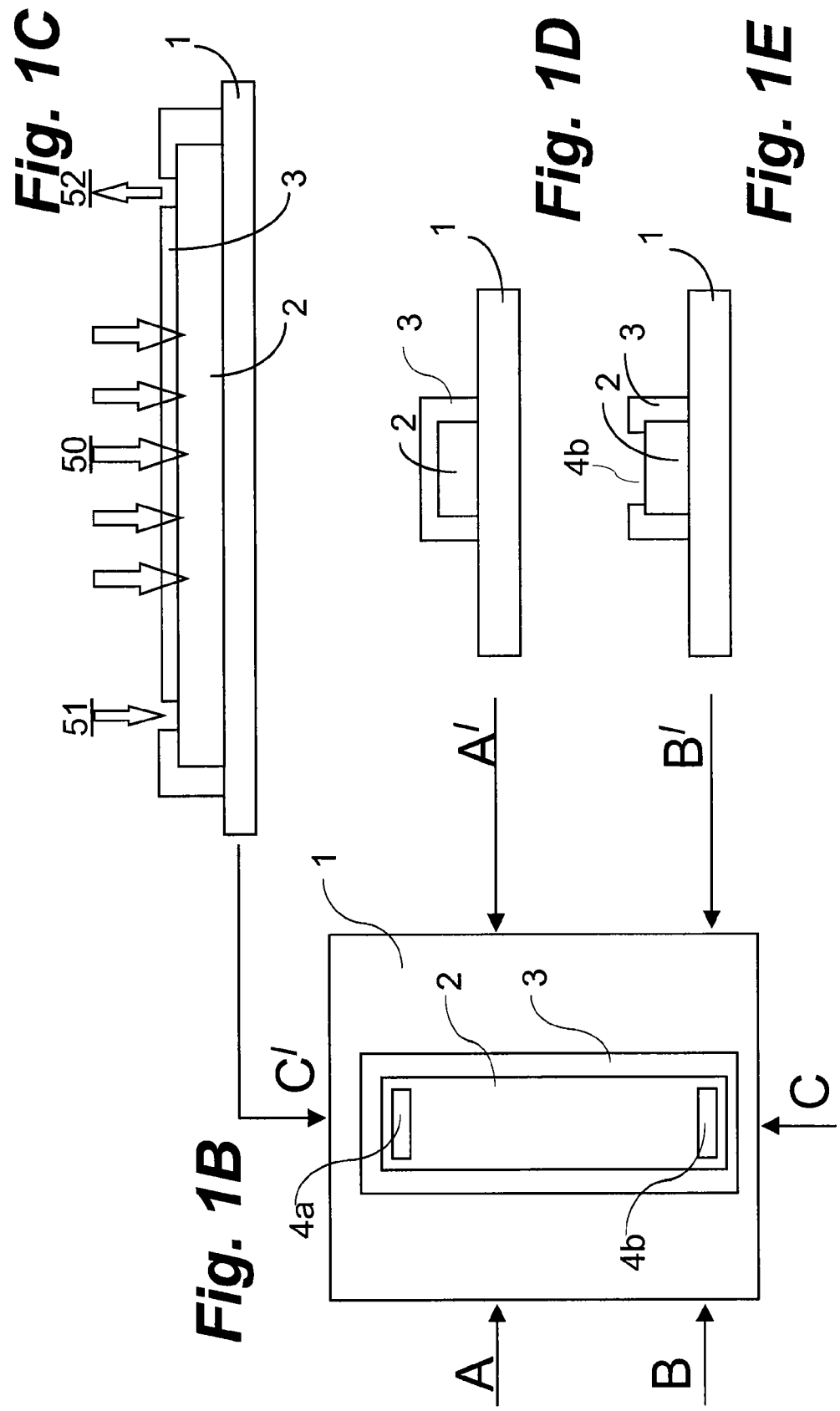

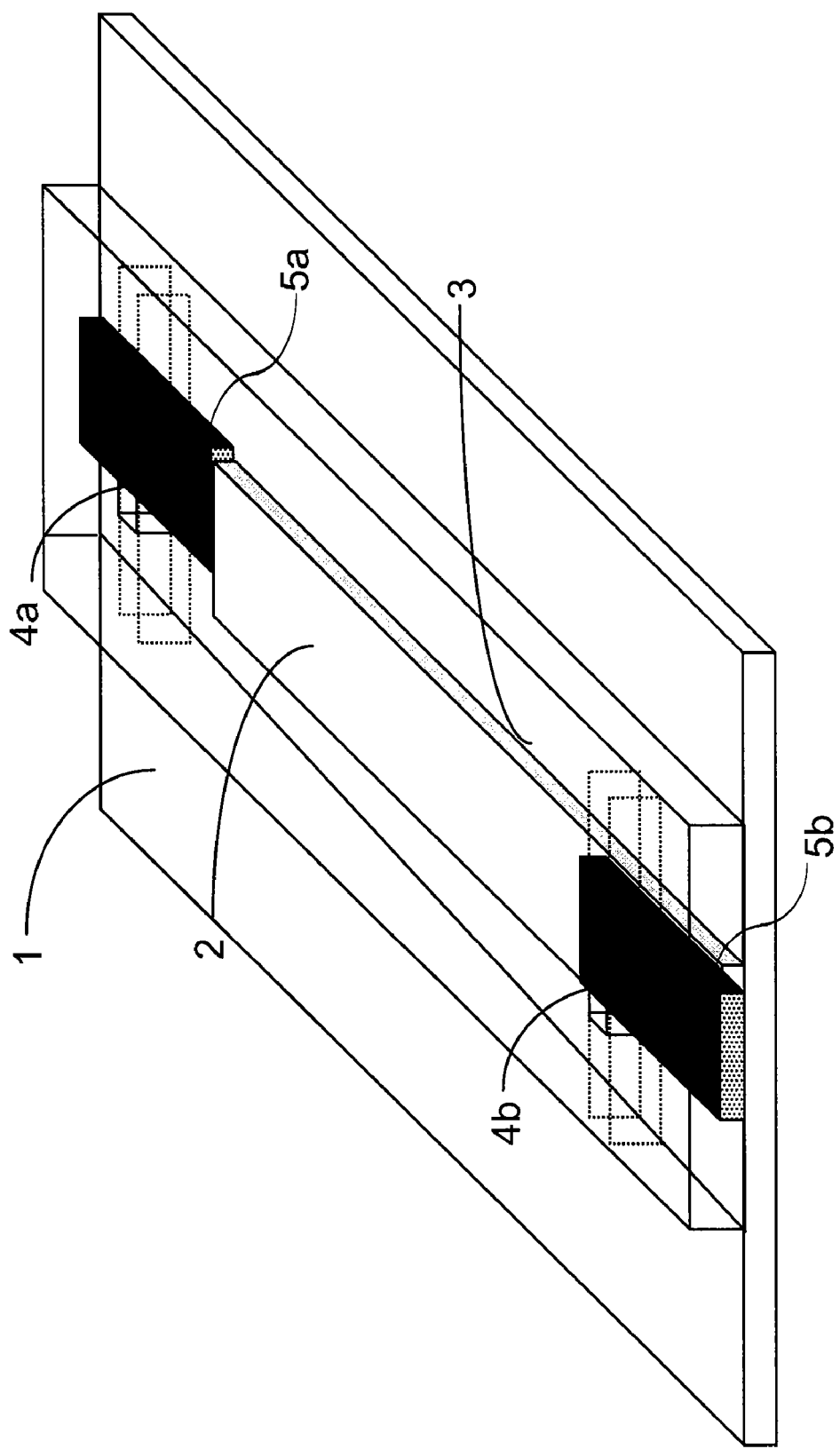

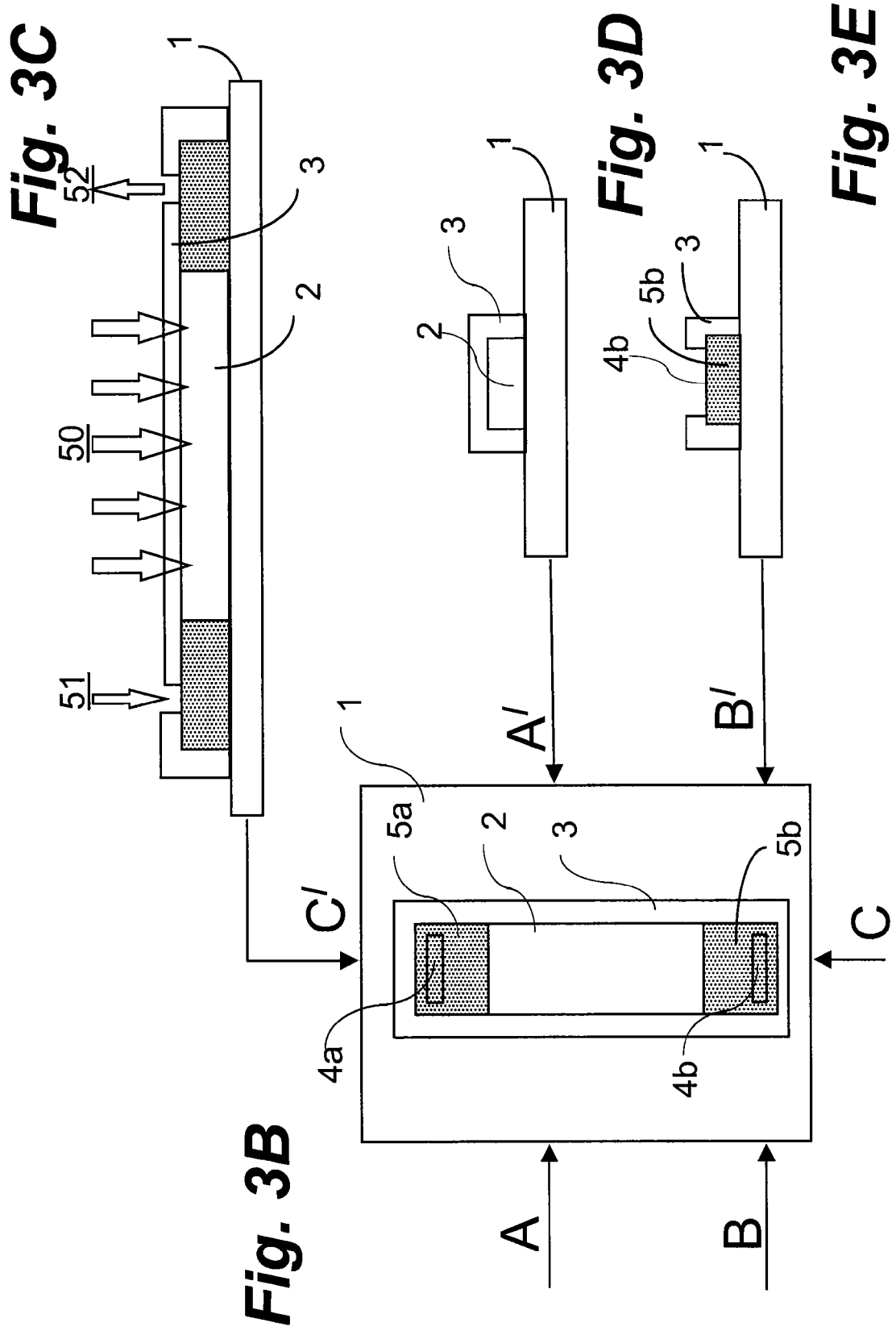

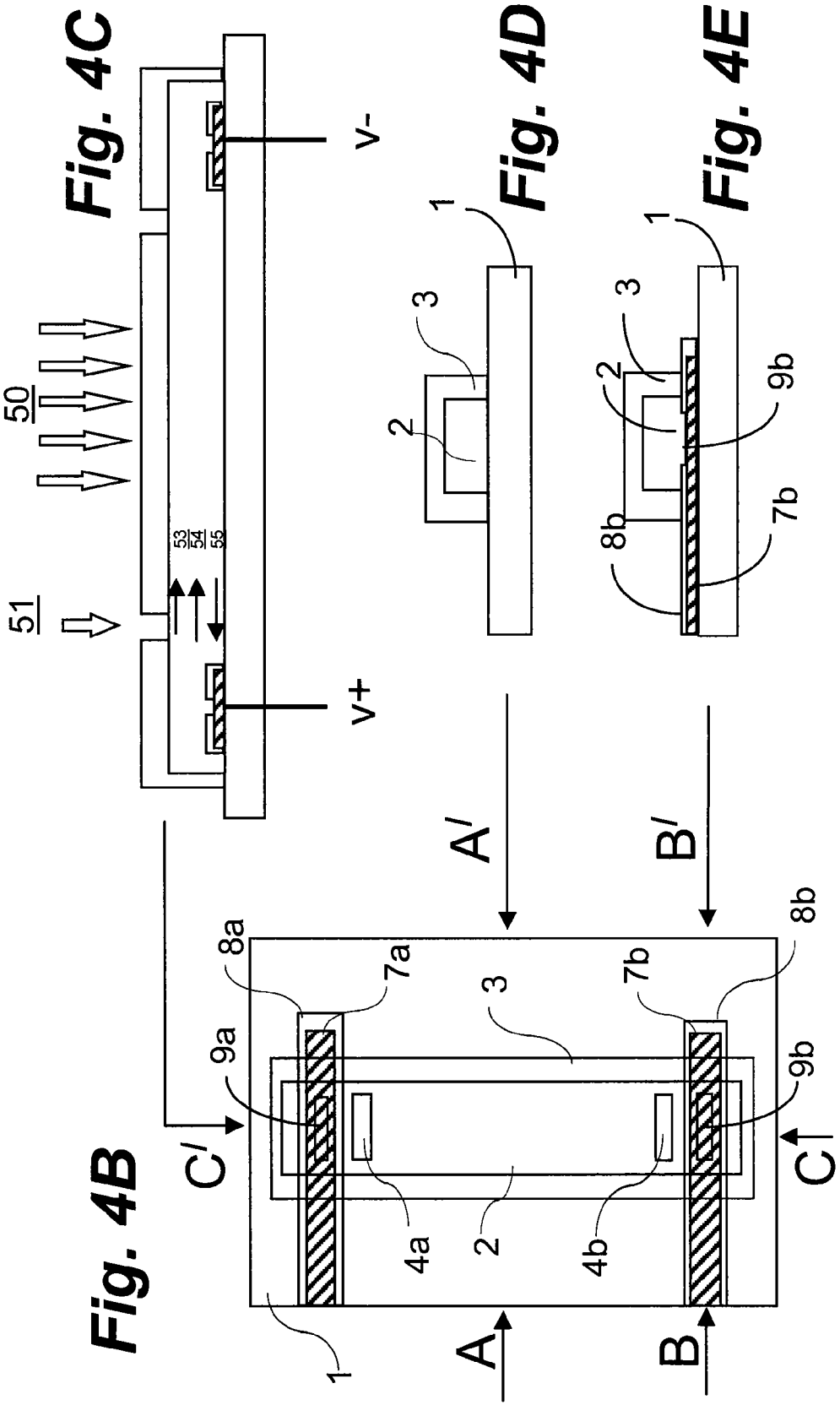

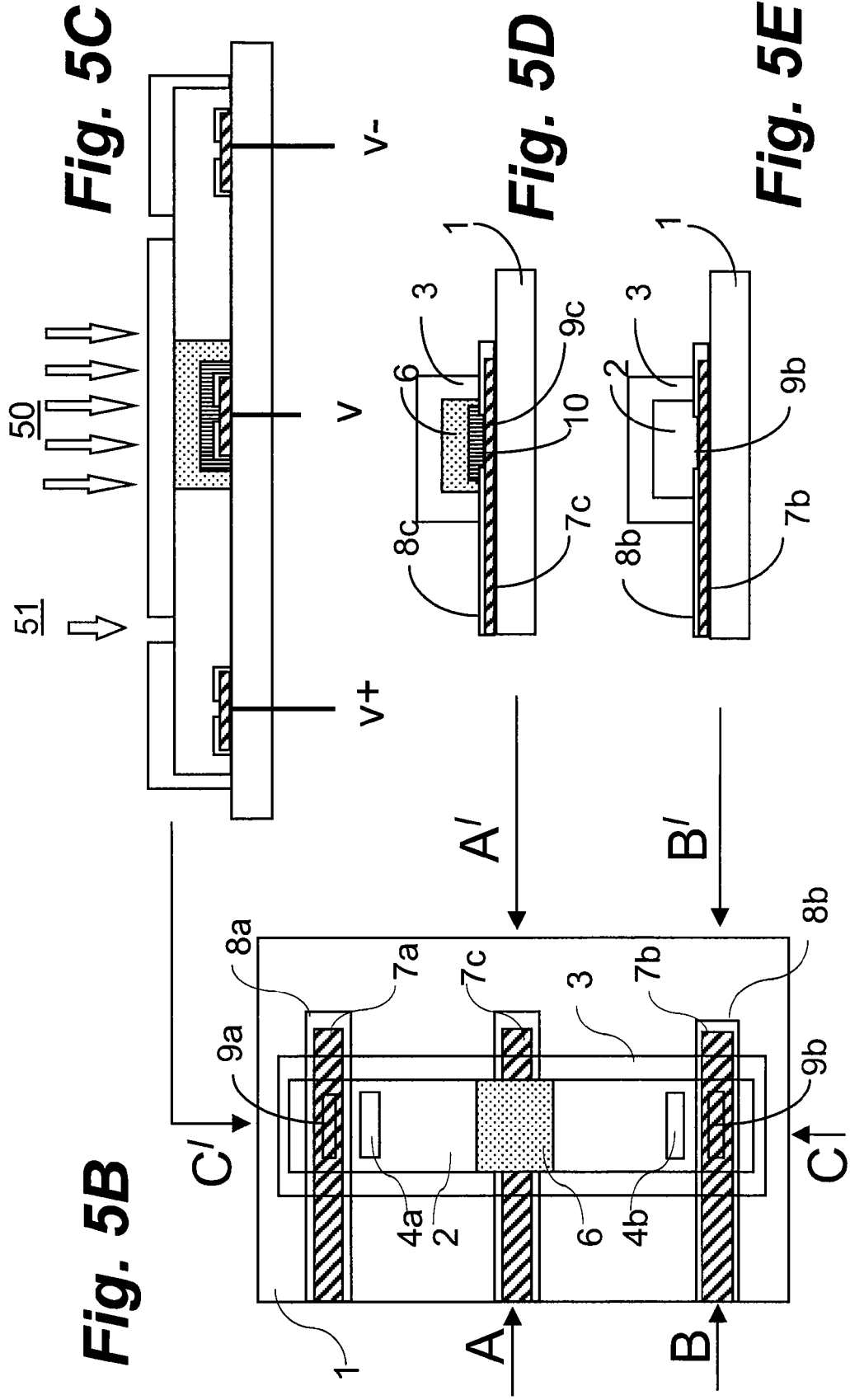

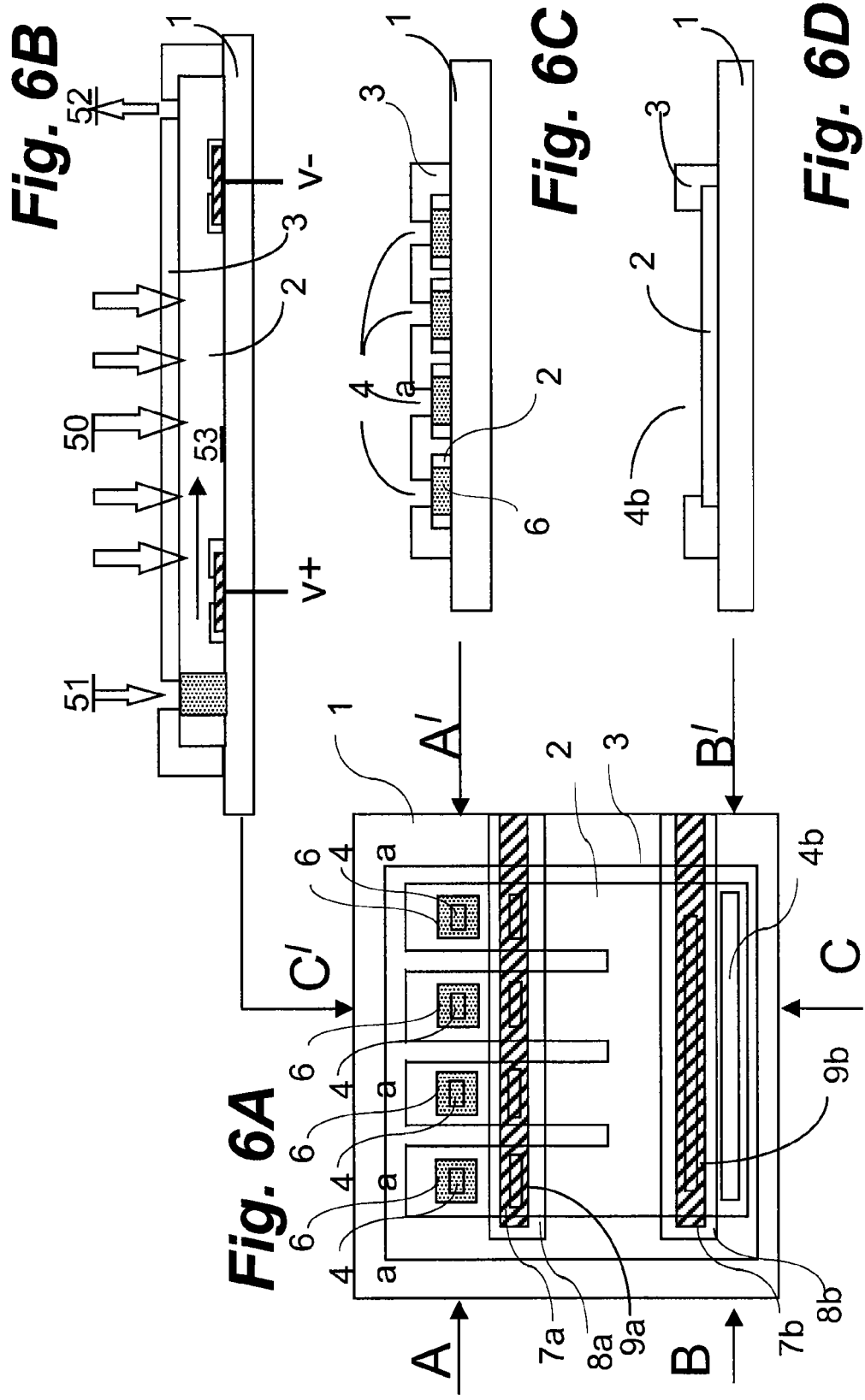

INTEGRATED ELECTROKINETIC DEVICES AND METHODS OF MANUFACTURE

REFERENCE TO RELATED APPLICATIONS

This Application is a divisional application of Parent Application U.S. Ser. No. 09/871,821, filed Jun. 4, 2001, issued as U.S. Pat. No. 7,214,300 entitled Integrated Electrokinetic Devices and Methods of Manufacture.

FIELD OF THE INVENTION

The invention is directed to devices with electrokinetic components for solute species transport and/or reaction and separation and their method of manufacture, for use in microscale analysis, mixture separation and reaction.

BACKGROUND OF THE INVENTION

Electrokinetic transport (electroosmosis, electrophoresis) of chemical species through thin slabs or through narrow conduits is known in the art. However, more recently, new devices with eletrokinetic-transport elements have been disclosed. In particular, devices described in the literature have been directed towards applications of eletrokinetic-transport technology in genomics, proteomics, combinatorial chemistry and high-throughput screening for drug discovery.

Electrokinetic-transport technology is used in species separation devices including slab-gel electrophoresis devices. In the slab-gel electrophoresis method, separation of chemical species occurs when the species in aqueous solution are transported at different rates along the gel. This class of prior-art devices generally consists of macro-scale slabs of hydrophilic-gel materials. Examples are described in U.S. Pat. No's. 4,574,040 and 4,663,015. In systems such as those described in the above referenced patents, pouring a gel-forming liquid into the space between two glass plates forms the slabs. The gel-forming liquid is an aqueous solution of hydrophilic polymers and cross-linkers. The gelation process causes the liquid to solidify into a solid slab. The resultant gel slab is a solid matrix containing a substantial quantity of water. The slab thickness is determined by the spacing between the plates maintained by spacer strips placed between and along two opposing edges of the plates. Clamps hold the plates together and the spacer strips are smooth so that a seal is formed under the pressure of the clamps, preventing leakage of either the gel-forming solution during gel casting or the buffer solution during electrophoresis.

Methods disclosed to reduce the dimensions of the transport channel of the slab-gel devices have generally used macrofabrication techniques. For example, U.S. Pat. No. 5,627,022 discloses a thin gel slab prepared inside a gel holder consisting of two planar substrates and a thin spacer consisting of beads in an adhesive matrix. Microfabricated multiple separation lane slab-gel devices have been disclosed, for example in U.S. Pat. No. 5,543,023. Such devices consist of an array of thin slabs separated by spacers. Multiple lane devices with gels cast into microchannel arrays are known in the art. U.S. Pat. No. 5,192,412 discloses a slab-gel contained within plates wherein one plate has a linear array of microchannels. U.S. Pat. No. 5,746,901 discloses a similar combination of corrugated and flat glass plates sandwiching gel slabs. U.S. Pat. No. 5,954,931 discloses an electrophoresis device with parallel channels formed by casting gel onto a substrate with microchannels. Gel compositions for small dimension electrophoresis gel slabs have been disclosed in U.S. Pat. No. 6,013,166. Macro-scale dried gel slabs that are reconstituted by treatment with water prior to use have also been reported in the prior art (U.S. Pat. Nos. 4,048,377 and 4,999,340).

Species separation devices of the prior art also include capillary tubes used both for capillary electrophoresis and capillary chromatography (for example U.S. Pat. No. 5,207,886). In this technique separations are conducted by electrokinetic flow of liquid through narrow-bore glass capillary tubes. In these prior-art capillary devices the separation occurs within the capillary tube and the separation medium is a liquid that fills the tube after it is introduced through one end of the tube. Some prior-art devices use a polymeric coating on the internal surface of the narrow-bore tube (U.S. Pat. Nos. 5,141,612 and 5,167,783), others use capillary tubes pre-filled with gel (U.S. Pat. No. 4,997,537), still others introduce the separation polymer dissolved in the sample liquid (U.S. Pat. No. 5,089,111).

Multi-lane separation devices consisting of multiple capillary tubes assembled in a housing have been disclosed in the art, for example U.S. Pat. No. 5,439,578. It is well known in the art that such capillary separation devices provide superior separation performance over slab-gel separation devices of the prior art because narrow bores provide for less spreading of the species in the separating medium. Also, because of superior heat dissipation, high voltages can be used to effect rapid separation.

Some shortcomings of these devices include the inability to easily integrate with other fluid manipulation elements or other elements of the analytical process and the inability to provide readily for variations of composition within the medium.

Integrated micro-analytical and micro-chemical-reaction devices, commonly also referred to as lab-on-a-chip devices, have been disclosed in the prior art (for example U.S. Pat. Nos. 4,908,112 5,126,022 and 5,180,480). These devices utilize micro-machining methods adapted from semiconductor chip manufacturing to fabricate micro or meso-scale devices on planar substrates for the purpose of performing separations, measurements and chemical reactions. These devices are mechanical structures realized by forming cavities and channels or trenches into a solid substrate. The devices are generally completed when a cover assembly over the cavitated substrate provides a cap that converts the cavities and channels into chambers and conduits. U.S. Pat. No. 5,429,734 however, discloses a channel etched into a semiconductor wafer that includes a monolithic capping means. U.S. Pat. No. 4,908,112 discloses separation devices including electrodes with channels etched into semiconductor slabs. U.S. Pat. No. 5,750,015 discloses separation devices with trenches formed in insulating plastic slabs. Other structures consisting of cavitation in planar substrates include devices with channels and detectors (U.S. Pat. Nos. 5,637,469 and 5,906,723), devices with chambers (U.S. Pat. No. 5,585,069) and devices with channels and mechanical sieving means (U.S. Pat. No. 5,304,487). Reactions, mixture separations and analyses take place in such microstructures in liquids that are electrostatically transported along the conduits. Generally in these prior art devices, the reactants, catalysts and reagents are stored and prepared in off-chip processes then introduced into the channels of the chip during use by pumping from one open end of the channel along its entire length. U.S. Pat. No. 5,126,022 discloses microfabricated trenches that are filled with gel prior to use.

Integrated micro-channel separation devices have been disclosed in the art, wherein electrokinetic fluidic manipulations are carried out in micro-channel structures more complicated than those feasible in a simple capillary tube with only an inlet and an outlet, and more complicated than an array of channels either in multi-lane slabs or capillary tube arrays. U.S. Pat. No 5,770,029 discloses a device with a main electrophoretic channel connected to a secondary, enrichment channel. U.S. Pat. No. 5,296,114 discloses an electrophoretic separating device consisting of a channel in the form of a loop with multiple inlet and outlet ports. U.S. Pat. No. 5,750,015 discloses a device consisting of a main trench and multiple branching trenches. Devices are disclosed with multiple connected channels (U.S. Pat. No. 5,800,690), intersecting channels (U.S. Pat. Nos. 5,599,432 and 6,010,608) and channels connected to multiple reservoirs (U.S. Pat. No. 5,858,195).

Integrated micro-channel devices in which there is a binding step combined with an electrokinetic transport step within a conduit or slab are also known in the art. U.S. Pat. No. 5,661,028 discloses a device that integrates a binding/primer element with an element for introducing reagents from off-chip for a Sanger sequencing reaction with an electrophoretic separation element consisting of a planar etched channel with glass cover plate backfilled with gel. U.S. Pat. Nos. 4,628,035 and 5,055,415 disclose antigen-antibody binding inside an electrophoretic medium.

The prior art of biosensors and dry reagent diagnostic devices contains numerous uses of hydrophilic materials or gels. Devices from this prior art that are made by microfabrication include for example U.S. Pat. No. 5,194,133 that discloses a biosensor with a micromachined channel filled with a gel material. Devices that consist of a composite of a gas-permeable layer and a hydrophilic-polymer layer also are known in the prior art of biosensors, including devices of this type made by microfabrication. For example U.S. Pat. No. 4,933,048 discloses a microfabricated gel and hydrophobic-vapor-permeable polymer for use as a salt bridge of a potentiometric reference electrode. U.S. Pat. Nos. 5,514,253 and 5,200,051 disclose micro-fabricated gas and enzyme biosensors that also utilize these composite layers. These numerous diagnostic devices disclosed in the prior art of biosensors utilize the gel or hydrophilic material as a medium for reagent retention or as an element through which species move by diffusion. However, none of these references teach the use of a layer composite of this general type in an active electrokinetic pumping application. Both the functional design and the mode of operation of this class of prior-art biosensor and dry-reagent diagnostic devices are different from active electrokinetic pumping devices.

Devices have been disclosed in the prior art that utilize voltages not for electrokinetic transport but for modulating the amount of hybridization at an electrode surface (U.S. Pat. Nos. 5,632,957 and 6,017,696) or for biological sample preparation (U.S. Pat. No. 6,129,828).

In summary, prior-art electrokinetic devices are either empty channels (trenches in planar substrates or conduits in tubes), channels with coated surfaces, or channels filled with polymer solutions or gel. Prior-art devices also include slabs of gels or gel tracks formed by casting gels into mechanical pre-forms or cavities. The prior-art devices are thus limited in one of several ways. Prior-art micro-channel devices, while manufactured in part by microfabrication methodologies, generally only provide for elements that contain mechanical structures. Thus they do not contain the chemicals and reagents required to function as truly integrated-analytical systems. At the current state of the art these types of devices consist of really only lab-glassware-on-a-chip rather than the complete lab-on-a-chip as they have been called. The prior art does not teach how the integration of chemical function can be accomplished with any generality. Furthermore, prior-art slab-gel based devices are generally made by traditional macro-fabrication methods, thus they are expensive to manufacture and use. They require large sample sizes and are slow in performance. They cannot easily be integrated either to provide multi-analysis capability, nor easily or cost effectively be combined with other components of an integrated analytical system.

Moreover, the materials of the transport element of prior-art slab-gel devices have been limited to gelatinous media. As such they are largely water-based and fragile and difficult to process into structures much more complicated than simple slabs. These materials are not amenable to planar processing nor microfabrication to make integrated devices. Thus there remains a significant need for cost-effective electrokinetic devices amenable to planar processing and/or microfabrication and for processes for their manufacture. A further need exists for electrokinetic devices with incorporated chemical entities.

SUMMARY OF THE INVENTION

It is an object of the invention to provide electrokinetic devices and a method of fabrication therefor, which devices are preferably applicable for use in micro-scale analysis, mixture separation and reaction.

It is yet a further object of the invention to provide electrokinetic devices including hydrophilic-matrix conductors for electrokinetic solute species transport and/or separation.

It is another object of the invention to provide electrokinetic devices that are suitable for planar processing and/or microfabrication.

It is still another object of this invention to teach methods whereby hydrophilic matrixes and included chemicals may be microfabricated.

It is a further object of the invention to teach methods whereby encapsulating elements can be microfabricated.

It is still a further object of the invention to provide electrokinetic devices featuring the integration of hydrophilic-matrix conductors with chemical entities contained in reservoirs and reaction regions to provide for self-contained micro-analytical systems. Chemical entities include separation polymers, attachment ligands or probes, primers, enzymes, filtration means, buffers and the like.

It is yet another object of the invention to provide devices that include self-contained reagents and are formatted as a cost-effective, single-use disposable device for use particularly in the fields of genomics and proteomics and molecular diagnostics.

Complex embodiments of devices in accordance with the present invention will in the following be collectively called integrated-electrokinetic circuits.

It is an object of the invention to provide integrated-electrokinetic circuits and their methods of manufacture.

It is an object of this invention to teach microfabrication methods for integrated-electrokinetic circuits that retain their chemicals during back-end processing steps. These objects of the invention are achieved in a device for electrokinetic transport of an aqueous solute, including an electrically insulating substrate; an electrokinetic conductor element in the form of a solid hydrophilic-matrix layer on the substrate, the matrix layer being in a substantially dry, inactive state and having a first surface engaging the substrate and a second surface; and a cover layer for electrically insulating and covering the second surface, the cover layer being impermeable to the solute; whereby exposure of the hydrophilic matrix to water converts the matrix from the inactive state to a hydrated, active state permitting electrokinetic transport of the solute.

In a preferred embodiment, the solid hydrophilic-matrix layer is in the form of a film that can be fabricated into a variety of micro-scale structures. The solid hydrophilic-matrix layer when hydrated functions as a conductor for electrokinetic species transport or separation.

In another embodiment, the device is manufactured in the form of a chip and further includes hydrophilic-matrix cladding containing chemical species adjacent to either an open conduit or a hydrophilic-matrix conductor, as well as other integrated microstructures for retaining chemical species for on-chip chemical reactions and integrated detection structures for on-chip species detection.

In devices in accordance with the invention, the transport of species, reactions, mixture separations and analyses takes place within hydrophilic-matrix conductors, within hydrophilic-matrix sheathed conduits, as well as within other formed elements such as reservoirs and reaction zones that consist of solid-state hydrophilic matrices into which water is introduced at or before the point of use.

Although reference is made throughout this application to transportation of a solute species, this term is intended to encompass transport of the solute species irrespective whether the solute is transported within the solvent or by way of a pumping of the solvent, for example by electroosmosis.

In another preferred embodiment of this invention, elements of integrated-electrokinetic circuits are produced by microfabrication. Thus, for example a particular circuit component of an integrated-electrokinetic circuit in accordance with this invention is a conductor for transport of a solute chemical species. The conductor preferably consists of a thin film of a solid hydrophilic-matrix material that has been patterned into a strip-line by a microfabrication method. This microfabrication is preferably performed on the hydrophilic solid in its dry or semi-dry form. The thin film is preferably less than 10 micrometers in thickness. Preferred dimensions of the strip-line are less than 100 micrometers in width and greater than 100 micrometers in length. In the preferred circuit, the solid hydrophilic-matrix conductor overlays a substantially planar substrate that is impermeable to the solute species to be transported through the hydrophilic conduit. The conductor is surrounded on its sides and top by a cover layer made of encapsulant materials also substantially impermeable to the transported species. In the preferred embodiment the encapsulant material is deposited by a film process and also is formed by microfabrication.

In still a further preferred embodiment of the invention, at least a portion of the insulating encapsulant material has the additional property that it is permeable to water vapor. This allows for the initially substantially dry and inactive hydrophilic matrices to rapidly take up water being transported through the encapsulant material as vapor. Upon exposure to water, the encapsulant retains the insulating properties that are required for the proper function of the device. The dry solid hydrophilic matrix however becomes a conducting electrolyte upon incorporation of water. The device is exposed to water either before or at the point of use of the device. In a variant of this preferred embodiment it is the substrate material that is water permeable.

In another embodiment of this invention, integrated-electrokinetic circuit components are provided where hydrophilic-matrix conductors, sheaths, reservoirs and reaction zones are prepared with in-situ chemical reagents for performing reactions, mixture separations or analyses. These in-situ chemicals are preferably introduced into the hydrophilic matrix at manufacture.

In still another embodiment, the device includes hydrophilic-matrix conductors in parallel arrays to facilitate transport of solute species through multiple lanes as might be used in a multiple sample separation on a single integrated device, or as might be used to transport chemicals to multiple reaction zones or multiple regions of ligand-binding. In yet an additional embodiment, the device includes hydrophilic-matrix conductors with intersections so as to facilitate movement of species from one conductor to another according to the timed application of voltages across the conductors.

In another embodiment, the device includes hydrophilic-matrix conductors that intersect but are isolated one from another to prevent electrical or solute species contact.

In a preferred embodiment the device includes hydrophilic-matrix conductors with integral electrodes. Thus for example, a particular circuit component of an integrated-electrokinetic circuit in accordance with the invention is an encapsulated hydrophilic-matrix conductor with integral electrodes for electrokinetic species transport. This circuit component can serve also as a column element in a separation device. The preferred device consists of a microfabricated hydrophilic-matrix conductor and microfabricated cover layer of encapsulant material.

The hydrophilic-matrix conductor preferably has one end through which a sample to be transported or separated can be introduced, and another end where the transported fluid flows out. The conductor is preferably disposed over microfabricated electrodes that provide the electromotive driving force to cause electrophoretic transport of charged species or electroosmotic flow of solvent. Solute species separation in the device of the invention occurs because of differential mobility of transported ions (as occurs in conventional slab-gel or capillary electrophoresis), or by differential residence at absorptive sites within a column element (as in conventional chromatography methods).

In a further embodiment of this invention, the device includes hydrophilic-matrix conductors with variable chemical composition along their length. In this embodiment, a hydrophilic-matrix conductor has a first region of a hydrophilic matrix interposed between two electrodes that provide the electrokinetic driving force. A second and third region are upstream and downstream of the first hydrophilic-matrix region. The hydrophilic matrix of the first region is composed of a material of high electroosmotic coefficient to maximize flow rate at a given applied voltage. The composition of the second and third regions is chosen to optimize for some other functional characteristic. For example a composition appropriate to perform a binding reaction, a separation or a species detection. Another example of this aspect of the invention is a hydrophilic-matrix separation element with graded pore size along its length.

In yet another preferred embodiment of this invention a reaction zone incorporating chemical entities for reaction is integrated with a hydrophilic-matrix conductor. A particular circuit component of the integrated-electrokinetic circuit is a reaction zone with inlet and outlet ports and means for transporting reactant chemicals and products respectively to and from the reaction zone.

In another embodiment of this invention, an integrated-electrokinetic circuit includes reagent reservoirs and waste reservoirs.

In still another embodiment of this invention, an integrated-electrokinetic circuit includes integral detectors, most preferably electrochemical detectors.

In a further embodiment of this invention a micro-analytical system features an integrated-electrokinetic circuit consisting of a number of different hydrophilic-matrix components. These include hydrophilic-matrix conductors, reservoirs, electrokinetic pumps, conductor junctions, integral electrodes, reaction zones and detectors. It is possible to perform numerous micro-analytical procedures using the device according to this invention. These procedures include ligand-binding assays, separations, PCR or primer extension reactions, as well as methods employing combinations of reactions and/or separations.

In another embodiment of this invention a micro-analytical system features a ligand-binding array with each binding element connected to an integrated electrokinetic pump consisting of hydrophilic-matrix conductors and integral electrodes. Target molecules in a sample solution are electrostatically pumped to a binding region as they pass through an orifice into the hydrophilic-matrix conductor. In this way the forced-convective flow of sample solution effects rapid species transport to the binding molecules within the binding layer. This device provides enhanced speed of response as well as better sensitivity compared to conventional ligand-binding arrays on non-porous substrates.

BRIEF DESCRIPTION OF THE DRAWINGS

The invention will now be further discussed in detail by way of example only and with reference to the following drawings, wherein:

FIG. 1B shows a schematic top plan view of the hydrophilic-matrix conductor of FIG. 1A;

FIG. 1C is a horizontal cross-section through the embodiment of FIG. 1B taken along line B-B';

FIG. 1D is a horizontal cross-section through the embodiment of FIG. 1B taken along line A-A';

FIG. 1E is a horizontal cross-section through the embodiment of FIG. 1B taken along line B-B';

FIG. 3A is a schematic perspective view of a hydrophilic-matrix conductor with solvent insoluble termini according to another embodiment of the invention;

FIG. 3B shows a schematic top plan view of the embodiment of FIG. 3A;

FIG. 3C is a horizontal cross-section through the embodiment of FIG. 3B taken along line B-B';

FIG. 3D is a horizontal cross-section through the embodiment of FIG. 3B taken along line A-A';

FIG. 3E is a schematic perspective view of a hydrophilic-matrix conductor with hydrophilic-matrix sheath according to an embodiment of the invention;

FIG. 4B is a schematic top plan view of the embodiment of FIG. 4A;

FIG. 4C is a horizontal cross-section through the embodiment of FIG. 4B taken along line C-C';

FIG. 4D is a horizontal cross-section through the embodiment of FIG. 4B taken along line A-A';

FIG. 4E is a horizontal cross-section through the embodiment of FIG. 4B taken along line B-B';

FIG. 5B is a schematic top plan view of the embodiment of FIG. 5A;

FIG. 5C is a horizontal cross-section through the embodiment of FIG. 5B taken along line C-C';

FIG. 5D is a horizontal cross-section through the embodiment of FIG. 5B taken along line A-A';

FIG. 5E is a horizontal cross-section through the embodiment of FIG. 5B taken along line B-B';

FIG. 6A is a schematic top plan view of an array of hydrophilic matrix conductors with integral electrodes and an array of reaction zones at each input orifice of the array of conductor elements, according to another embodiment of the invention;

FIG. 6B is a horizontal cross-section through the embodiment of FIG. 6A taken along line B-B';

FIG. 6C is a horizontal cross-section through the embodiment of FIG.6A taken along line A-A';

FIG. 6D is a horizontal cross-section through the embodiment of FIG.6A taken along line B-B';

DETAILED DESCRIPTION OF THE PREFERRED EMBODIMENTS

Throughout the following description, equivalent elements are referred to by the same reference numbers.

Figure 1A:
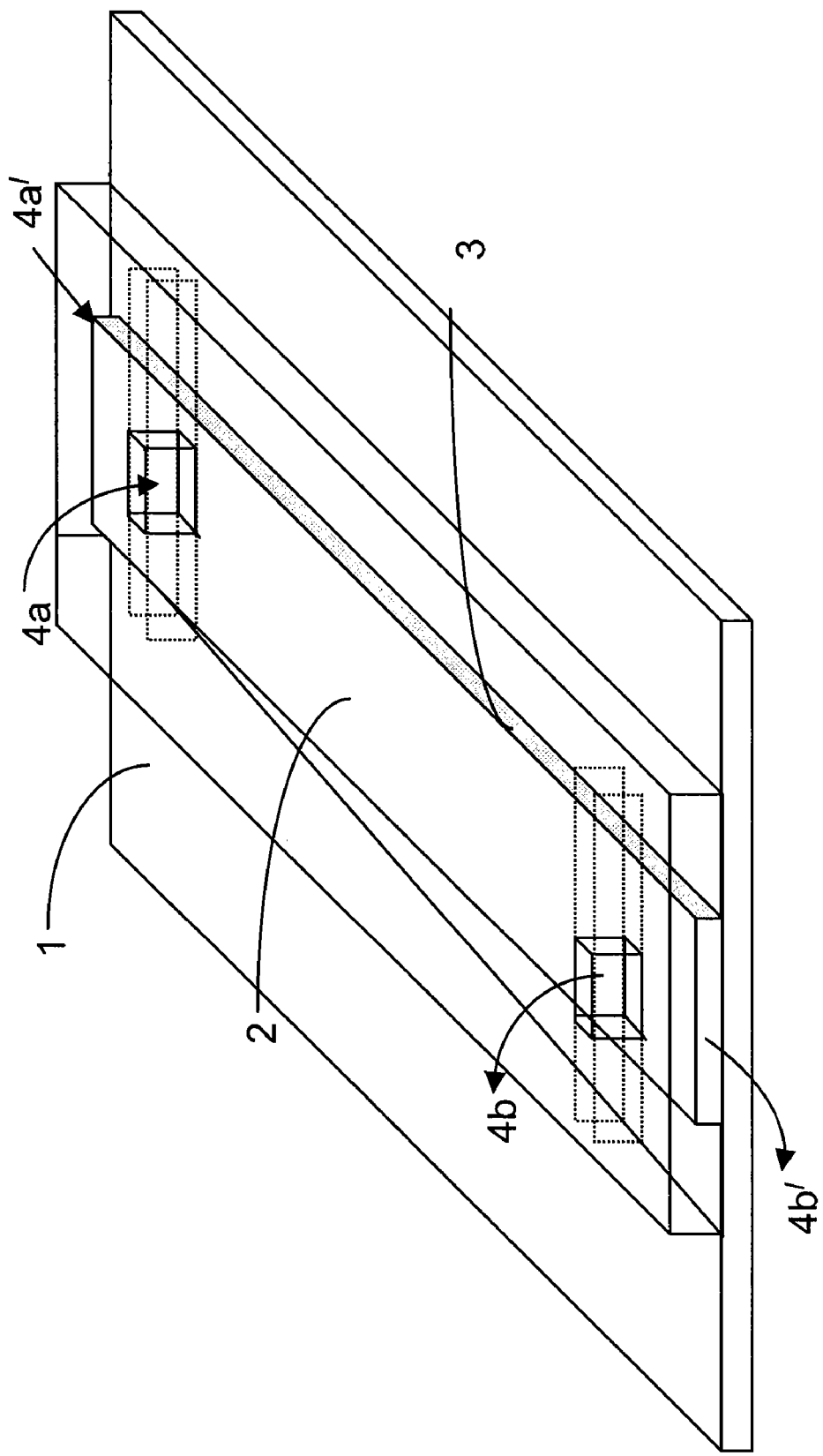
FIG. 1A is a schematic perspective view of a hydrophilic-matrix conductor according to a preferred embodiment of the invention.
Figure 2:
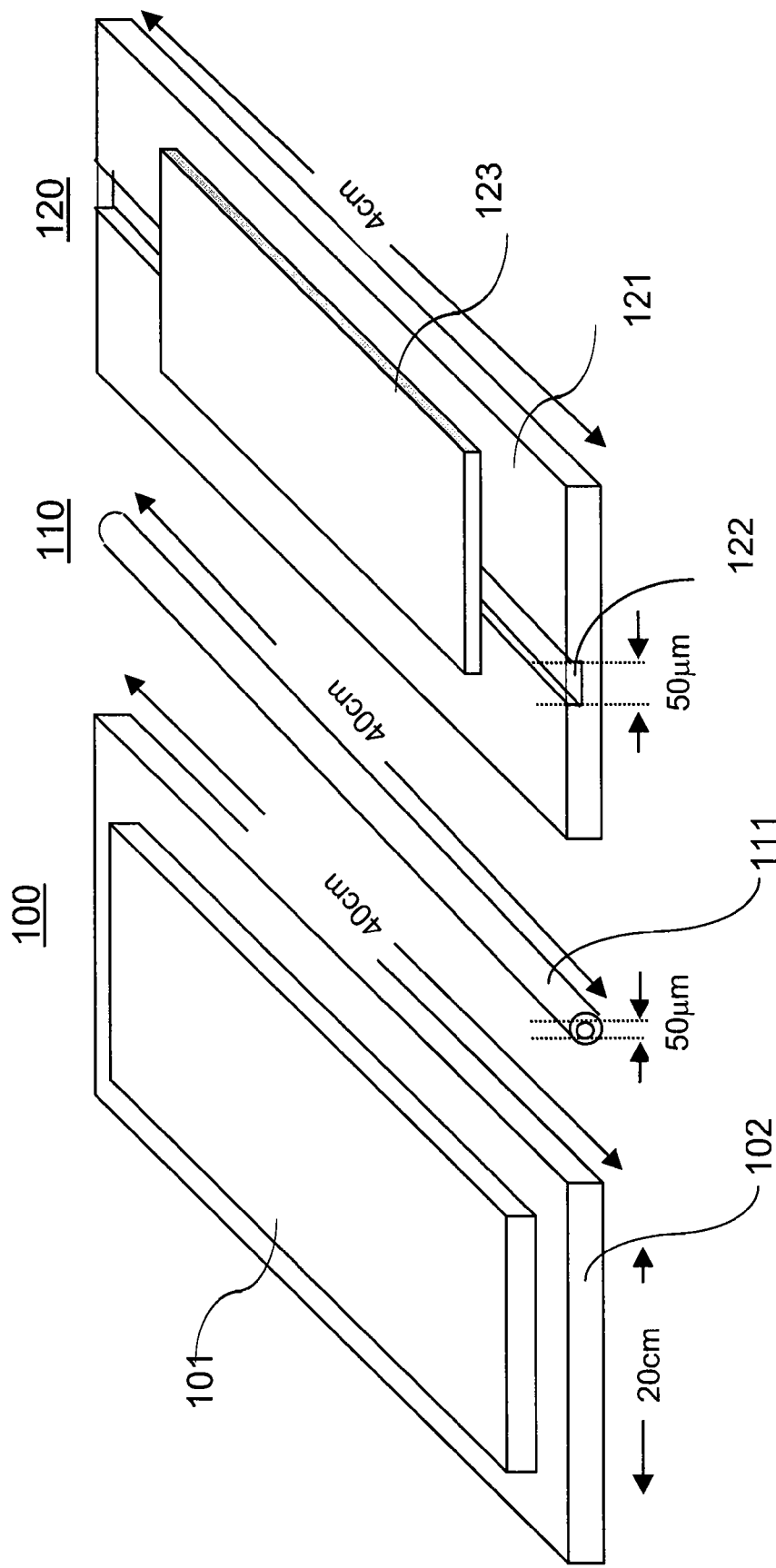
FIG. 2 is a diagram of various prior art devices.

FIGS. 1A and 1B are respectively a perspective view and a plan view of a first embodiment of the invention. Cross-sections through this embodiment are shown in FIGS. 1C and D. FIG. 2 shows for comparison electrokinetic-transport devices of the prior art.

The device of FIGS. 1A and 1B consists of a planar insulating solid substrate 1, and an overlayer of a solid hydrophilic-matrix material 2. Matrix layer 2 is spatially defined as a strip-line with a longitudinal dimension and provides an electrolyte conductor along which chemical solute species can be transported. The conductor 2 is covered by a cover layer 3 of a water vapor-permeable material and has openings 4a and 4b that allow the entry and exit of solute species to be transported through the conductor. Openings 4a and 4b are shown as located at either end of conductor 2. Also possible are passages through the water permeable layer, as shown by 4a' and 4b' in FIG. 1. Also possible are openings through the side or lower surfaces. The conductor 2 is connected to other elements of the device through openings 4a and 4b. Thus in some uses of the conductor of this embodiment it may be connected to a test solution at one end through 4a and a reservoir at the other through 4b. Solute species can be electrostatically pumped through 4a from the test solution into the conductor, then along the conductor to the reservoir through 4b. In other uses of the conductor of this embodiment 4a and 4b may be connected to other hydrophilic-matrix conductors or to other microfabricated elements such as reaction zones, reservoirs and the like as part of an integrated-electrokinetic circuit.

Referring to the B-B' cross-section of FIG. 1C, in operation a portion of the top surface of the device is immersed in an aqueous medium. Water 50 is transported as its vapor through the water vapor-permeable cover layer 3, into the initially dry, inactive hydrophilic solid matrix 2. The cover layer 3 is otherwise insulating i.e. it does not transport other solute species, ions or electrons. After water has been absorbed into the matrix 2, it is rendered functionally equivalent to an aqueous electrolyte. Species 51 that are introduced into the wire through opening 4a, or dry solid reagent initially present in the hydrophilic matrix at manufacture, can move through the wire by electrokinetic transport through conductor 2 when excited by application of a voltage. Species 52 exit the conductor 2 at opening 4b. The voltage is applied by two spaced apart electrodes (not shown) that make electrical contact to the hydrophilic-matrix layer. Such electrical contact means are well known to those skilled in the art. They include electrodes in the form of contacting pins that are brought into electrical contact with the electrokinetic-conductor layer on the substrate, as well as integral electrodes described further below.

The specific composition of the material of layer 2 depends on its function in the device. The primary function of the hydrophilic-matrix material is to provide for a physical support structure into which water can be incorporated to render the layer functionally an aqueous electrolyte. In separation applications described in later embodiments of this invention, the conductor is used as a separation column. In these applications the composition of the conductor layer 2, is selected to provide optimum separating properties that are determined by the shape and size of the species to be separated. In applications where a high flow rate of solution through the conductor is the important property then the composition is chosen to maximize the electroosmotic coefficient.

The hydrophilic-matrix 2 consists of a material composed of either monomeric or polymeric hydrophilic molecules that readily incorporate water. Examples are sugars, starches, alcohols, ethers, poly amino acids proteins and hydrophilic silanes and derivitized silanes. The hydrophilic matrix 2 may consist of a hydrophilic polymer in an extended state such as in a gel. Absorption of water results in a gel-like polymer in which water is incorporated into polymer chain interstices. Examples of suitable materials are cross-linked polyvinyl alcohols, poly hydroxy methacrylates, polyacrylamides, agarose, gelatins and silanes. The hydrophilic matrix 2 may be formed from a latex. The hydrophilic matrix may also contain dry electrolyte salts (to achieve high internal osmolality for good water uptake), buffers (to regulate internal pH for control of swelling of the hydrophilic matrix and to regulate internal pH to control chemical species transport and reaction) and other reagents depending on the function of the device in which the conductor is used.

The water vapor-permeable layer may be manufactured from a variety of different materials. Low density, hydrophobic hydrocarbon and fluorocarbon polymers are insulating and water permeable. Silicones, siloxanes, silicone-polycarbonate copolymers are preferred materials because they are insulating and highly water vapor permeable. The most preferred materials are dimethyl polysiloxane and silicone polycarbonate because they can endure a significant physical expansion of the underlying material as water is absorbed.

The device of the embodiment of FIG. 1 is fabricated using microfabrication technology. For example the substrate 1 may be any planar material suitable for use in microfabrication equipment such as silicon, a ceramic, a glass or a polymer. The substrate material can be insulating as is, or it can be coated with a material to render it insulating. For example, if the substrate is semiconducting silicon it can be coated with insulating silicon dioxide according to numerous techniques well known in the art. The substrate may be partially manufactured, in which case it already supports microfabricated conduits and chambers with insulating coatings, and a next level of electrokinetic circuitry is being fabricated. Some methods of microfabricating hydrophilic solid matrix layers that are appropriate to their use in biosensors are well known in the prior art of biosensors. Compositions and methods which can be used for microfabricating hydrophilic-matrix layers for the electrokinetic devices of this invention are not known in the art In one embodiment of the manufacturing method of the current invention, photo-formable formulations are used for the manufacture of the hydrophilic matrix. Additives to hydrophilic polymer materials that cause cross-linking upon exposure to radiation are well known. Such additives when formulated with the other components of the hydrophilic matrix in accordance with the invention render the cast polymer film photo-formable. The process of photo-forming is similar to the processing of a standard photoresist. A layer of the material is deposited on a planar substrate by spinning, spray printing, dipping or casting. It is allowed to dry. The dried layer is exposed to actinic radiation through a mask. UV exposure is common, although other wavelengths of light are possible depending on the additive component's wavelength sensitivity. Electron beam formable materials also are feasible. The exposed film is then developed in a developing medium in a bath, or spray or even a dry plasma process. For the wet development processes aqueous developing solutions are typically used. It is a disadvantage of such a process that salts and other chemicals that might be necessary for the proper operation of the device would be removed from the hydrophilic matrix during the wet development process. Another disadvantage of photo-formable layers is the potential deletereous effect on the intended properties of the final hydrophilic matrix of the photo-active additives.

A preferred embodiment of the manufacturing method, a more general approach to photo-forming hydrophilic-matrix layers, is disclosed here. This process is particularly suited to processing of hydrophilic-matrix materials containing salts and other dissolvable reagents for the electrokinetic-conductor applications of the current invention. The process utilizes completely dry plasma etching steps on hydrophilic materials designed to be ash free when plasma etched.

By way of example, a hydrophilic-matrix material containing electrolyte salts and buffers is deposited on a planar substrate from an aqueous solution by spinning, spraying, printing or dipping. Spinning is preferred. A photoresist layer is coated from a non-aqueous solvent over this. It is exposed and developed. The photoresist pattern is then transferred by etching into the underlying hydrophilic-matrix material using a plasma process that leaves no ash in the etched areas. The plasma etch step concurrently removes the photoresist layer. For example, when the hydrophilic matrix contains only carbon, hydrogen, oxygen and nitrogen an oxygen plasma will etch the material forming only volatile etch products and no ash. In this example the hydrophilic matrix should be formulated with non-metallic salts and buffers to be ash-free during oxygen plasma etching. Thus the preferred compositions of the hydrophilic matrix and its electrolytes, buffers and reagents are those suitable for ash-free plasma etch processing. Using the above described ash-free dry processing techniques one or more hydrophilic layers may be sequentially processed into formed structures without exposure to wet developers. All of the components of the films are retained during the process. No potentially deleterious additives are required.

The water vapor permeable cover layer 3 may be deposited from the vapor phase using techniques well known in the microfabrication art such as sputtering, plasma deposition, or glow discharge polymerization. Preferably however, the water vapor permeable layer is deposited from solution. Solvent-castable material compositions such as silicones, siloxanes or silicone polycarbonates are thus preferred. The cover layer 3 is preferably photo-formed or patterned using a standard photolithography and subtractive etching method.

Those skilled in the art will appreciate that devices in which there is rapid water absorption into the dry hydrophilic matrix could also be fabricated by making the insulating substrate 1, or an insulating coating on it, out of a water-permeable material. In general, devices with any suitable arrangement of a water-permeable insulating material in contact with at least a portion of the dry hydrophilic matrix will facilitate wet-up of the hydrophilic matrix.

It will be apparent to those skilled in the art of lab-on-a-chip devices that it is possible to configure the single conducting element of the embodiment described in FIG. 1 as part of a more complex integrated-electrokinetic circuit. It is well known to practitioners of integrated-circuit technology that the methods of planar microfabrication such as those disclosed for the fabrication of the embodiment of FIG. 1 are particularly suited to the fabrication of more complex structures such as the integrated-electrokinetic circuits disclosed herein. The conductor of the embodiment of FIG. 1 may be a component of a device consisting of an array of such conductors integrated on a single planar substrate. Such an integrated-electrokinetic circuit will be useful in numerous micro-chemistry applications. The array can be used to perform numerous separations at the same time, or the it can be used to transport numerous micro-batches of test solutions to arrays of reaction zones to perform multi-analyte assays at the same time. Another example is an integrated-electrokinetic circuit having intersecting and contacting conductor elements so that aliquots of solution being transported down one conductor can be electrostatically transferred to another. Even complex conductor geometries of these types of devices can be readily fabricated through a single photo-process step of the hydrophilic-matrix conductor layer, a so-called single-level process. An integrated-electrokinetic circuit can also consist of conductor elements that intersect but are isolated one from another. In this example of a two-level conductor process, a first hydrophilic-matrix layer is formed into a conductor element by photolithography. The conductor is coated with an insulating layer, photo-processed to cover the first hydrophilic matrix and to form openings, then a second hydrophilic-matrix layer is formed and photo-processed into a conductor element that crosses the first conductor but is separated from it by the insulator. Finally there is a second insulator coating on the second conductor level. Further examples of integrated-electrokinetic circuits are described in the embodiments of FIGS. 5 and 6.

FIG. 2 shows schematics of prior art electrokinetic devices. As was discussed in the background to this invention, there are three categories of prior-art devices. Schematic 100 shows some of the functional components and general dimensions of prior art slab-gel devices. In contrast to the devices of this invention they are produced by macro-fabrication methods. The devices are prepared by casting a gel slab 101 onto a plastic or glass support 102. Prior-art devices such as these are presented for use with the gel in its wet form.

Schematic 110 shows the general form and typical dimensions of a prior-art capillary tube used for capillary electrophoresis. The prior art capillary tubes are glass pipes with circular cross-section.

Schematic 120 shows the general form and typical dimensions of planar micro-channel devices of the prior art. Capillary sized channels 122 are formed into planar slabs of insulator 121 and capped with an insulating cover 123. The resulting cavity closely emulates the cross-sectional dimensions of the prior-art capillary tube.

In contrast to the devices of the current invention, devices 110 and 120 of the prior art are empty pipes or channels into which electrolyte is introduced at the point of use through one of the open ends of the pipe and the capillary is filled by pumping of the fluid along the length of the pipe prior to the electrophoretic separation.

FIGS. 3A-D show a further embodiment of the invention. The Figures respectively illustrate a perspective view and a plan view with horizontal cross-sections A-A' and B-B' of a conductor consisting of a hydrophilic-matrix conductor with insoluble termini. In FIGS. 3A-D the device consists of a planar, insulating solid substrate 1, an overlayer of a hydrophilic-matrix material 2. Hydrophilic-matrix layer 2 is spatially defined as a strip-line with a longitudinal dimension along which species can be transported. It is delimited at either end by insoluble termini 5a and 5b that are made of a hydrophilic-matrix material that does not dissolve in water. The cover layer 3 of water vapor-permeable material includes openings 4a and 4b that allow the entry and exit of solute species to be transported through the conductor. Openings 4a and 4b are located at the position of the termini 5a and 5b.

Referring to the B-B' cross-section of FIG. 3C, in operation a portion of the top surface of the device is immersed in an aqueous medium. Water 50 is transported as vapor through the water vapor-permeable cover layer 3 into the initially dry, inactive hydrophilic-matrix 2 (as in the case of the FIG. 1 embodiment). The cover layer 3 is otherwise insulating, that is, it does not transport other solute species, ions or electrons. The terminal regions 5a and 5b which are intended to come into direct contact with aqueous media (either during use of the device or during back-end manufacturing process steps) provide a barrier so that contents of the hydrophilic-matrix material 2 do not dissolve out into the aqueous media. For example, layer 2 may contain polyethylene glycol. Then, termini 5a and 5b may be made of a cross-linked polymer that is impermeable to polyethylene glycol. The function of the termini 5a and 5b is to allow electrokinetic transport into the conductor 2 of selected species in the aqueous medium 51 (solute for transport to a reaction, species to be separated or detected) through opening 4a while preventing efflux of larger molecules that are fabricated into the matrix of conductor layer 2. These molecules are retained within the conductor layer 2 during the course of the device's operation. Species 52 exit the conductor through opening 4b.

The embodiments of FIG. 3A-3D (as well as the embodiments of FIG. 3E and FIGS. 5 and 6) shows examples of devices with hydrophilic-matrix layers formed with different compositional regions. Those skilled in the art will recognize that the ability to fabricate electrokinetic conductors with regional compositional variations could be advantageous in other applications of these devices. Practitioners of the art will also recognize that advantageous compositional variations of the electrokinetic transport medium are difficult to realize in the bulk cast slab-gel devices or in the empty capillary pipe or channel devices that are filled with transport medium by pumping along the length of the pipe or channel at the point of use. One example of the prior art where regional compositional variation has been achieved is the macro gel-slab used in prior-art two-dimensional protein separation devices. The macro gel-slab is fabricated with its composition varying in a direction orthogonal to the electrokinetic transport direction. This compositional variation is designed to effect a spatially dependent pH orthogonal to the transport direction. Such materials are suited to two-dimensional separation of proteins by virtue of the pH dependence of the protein molecules' charge and hence electrophoretic mobility. A micro-scale device of this type or an integrated array of such devices can be fabricated using the technology of the current invention.

In another example, the hydrophilic-matrix conductor has a regional variation of pore size along the transport direction. This property will cause there to be regional variation of electrokinetic mobility of transported species. This is advantageous in a separation device where the species to be separated have a wide range of mobilities. In a uniform-pore separation medium, high molecular weight molecules will neither be transported far nor well separated in the time it takes small molecules to traverse the full length of the medium. In a graded-pore device these differences will be reduced. Such a compositional variation can be effected readily using microfabrication technology. In one technique a hydrophilic matrix layer is formulated with radiation induced cross-linkers as in a standard photoresist. The degree of cross-linking is dependent on the radiation dose, also as in a standard photoresist. Different regions of the layer when exposed to different degrees will give differently cross-linked regions. Less cross-linked regions will have larger pores and higher mobilities, highly cross-linked regions smaller pores and lower mobilities.

In some uses of hydrophilic-matrix conductors according to this invention it might be advantageous to provide for a rapid conducting path in species contact with an adjacent material such that species can inter-diffuse between them. Such a device is shown in FIG. 3E. It is still another example of a device with compositional variation of its hydrophilic-matrix materials. There is a microfabricated hydrophilic-matrix conductor 2 with a cladding layer of a second hydrophilic-matrix material 5 running along its length and in contact with it. Both hydrophilic-matrix layers are coated with a water-permeable insulating cover layer 3. As in the FIG. 3A example, electrokinetic transport of species is primarily along conductor 2. Hydrophilic matrix 5 may contain absorption sites for retention of species traversing the conductor 2 during the use of the device in an electrokinetic chromatographic separation application. Hydrophilic matrix 5 may contain reagents (salts, buffers or polymers and the like) that, when released into conductor 2, regulate the transport properties through the conductor. In the FIG. 3E embodiment, the cladding layer 5 is first formed on substrates, then conductor 2 is deposited onto it and microfabricated to be co-linear with 5. There are clearly other spatial arrangements of the two hydrophilic matrix layers that will provide equivalent function as the embodiment of FIG. 3E. For example, it is possible to first microfabricate layer 2 and then layer 5 so that layer 5 is on top of layer 2.

Figure 4A:
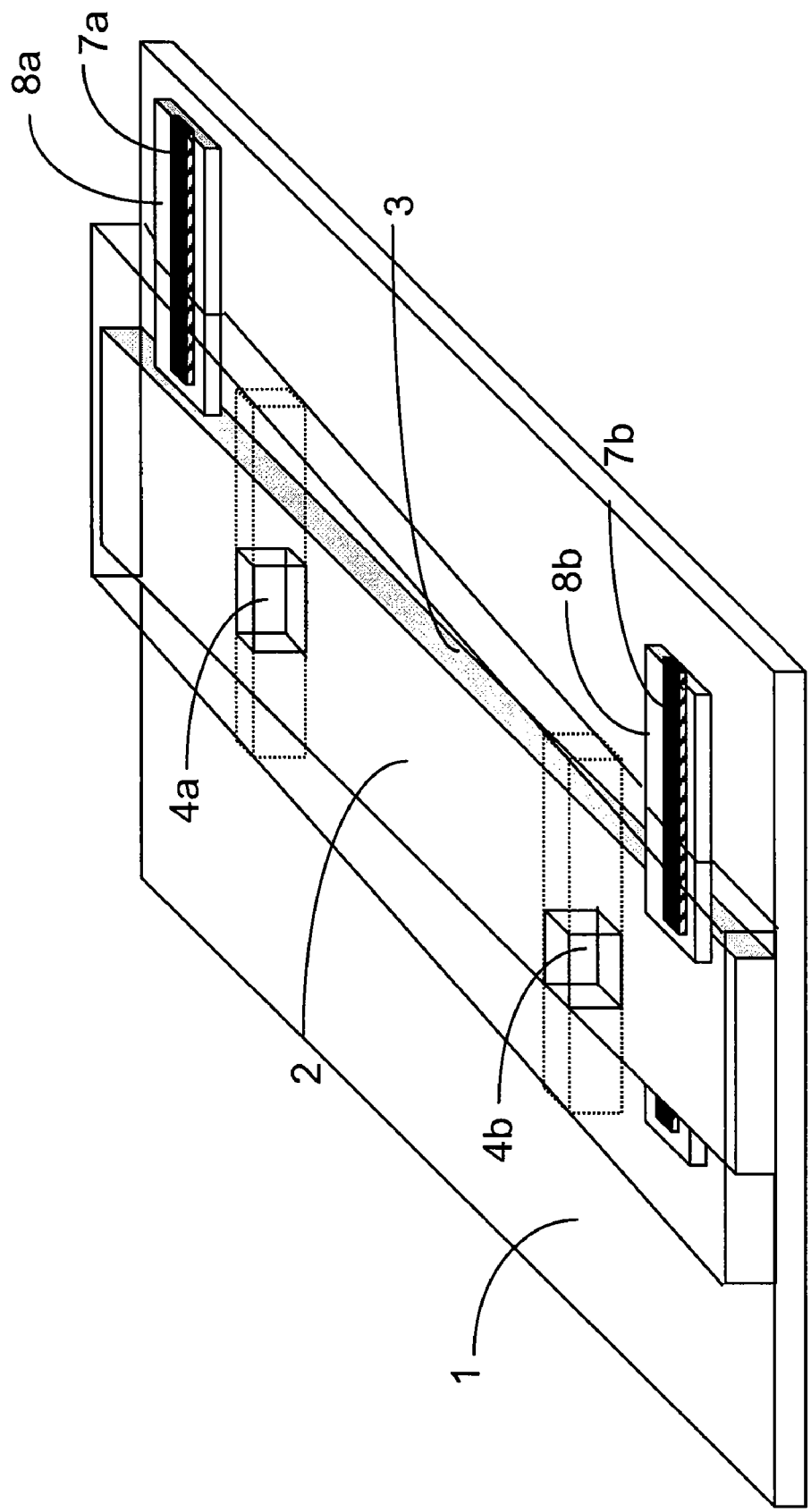
FIG. 4A shows a schematic perspective view of a hydrophilic matrix conductor with integrated electrodes according to a further preferred embodiment of the invention.

FIGS. 4A-E show another embodiment of the invention. The Figures respectively illustrate a perspective view and a plan view with horizontal cross-sections A-A' and B-B' and C-C' of a hydrophilic-matrix conductor with integral electrodes. In FIGS. 4A and 4B the device consists of a planar, insulating solid substrate 1 with two electrodes 7a and 7b spaced apart on the surface of the substrate. Electrodes 7a and 7b are electrically insulated by layers 8a and 8b along the length of the electrodes. The conductor 2 is in the form of an overlayer of a hydrophilic-matrix material applied to the substrate and spatially defined as a strip-line with a longitudinal dimension along which species can be transported. Spaced apart portions of the conductor layer 2 are located over the spaced apart electrodes 7a, 7b so that the electrodes are at different positions along the long dimension of the layer 2. Passages through the insulators 8a and 8b are provided at locations 9a and 9b that permit electrical contact between electrodes 7a and 7b and the conductor layer 2. In use, the other ends of electrodes 7a and 7b (not shown in the diagrams) are connected to electrical circuits that supply electrical power to the electrodes. A cover layer 3 of a water vapor-permeable material is applied over the conductor layer 2. There are openings 4a and 4b that allow the entry and exit of species to be transported through the conductor.

Referring to the C-C' cross-section of FIG. 4C, in operation a portion of the top surface of the device is immersed in an aqueous medium. As in the case of the embodiment of FIG. 1, water 50 is transported as its vapor through the water vapor permeable layer 3 into the, initially dry, inactive hydrophilic solid matrix 2. The cover layer 3 is otherwise insulating, that is, it does not transport other solute species, ions or electrons. These molecules are retained within conductor layer 2 during the course of the device's operation. After water has been absorbed into the matrix 2, it is rendered functionally equivalent to an aqueous electrolyte. Species 51 introduced into the conductor layer through opening 4a, or dry solid reagent initially present in the hydrophilic matrix at manufacture, become transportable by convective flow of the electrolyte within conductor layer 2 when electrostatically pumped, or when the solutes are electrically charged, by electrophoretic transport in an electric field. The application of an electrical potential difference between electrodes 7a and 7b provides the electromotive force for electrokinetic transport of species. Positively charged species 54 will drift towards the cathode, negatively charged species 55 towards the anode. Also, the entire aqueous electrolyte within the hydrated hydrophilic matrix will be pumped by electroosmosis. As is known in the art, the zeta potential of static surfaces within the solid matrix and its walls is generally negative and the flow of the body of electrolyte 53 within the matrix 2 will be toward the negative electrode as shown in FIG. 4C.

Electrodes 7, insulators 8 and passages 9 are manufactured by standard micro-fabrication methods. Preferably the compositions and methods of manufacture of these structures are taken directly from standard processes employed in high volume manufacture of silicon chips. Thus electrodes 7 are polysilicon or refractory metal, or refractory metal suicides or gold, for example. Insulator 8 is silicon dioxide or polyimide, for example.

Those skilled in the art will recognize that there are other possible arrangements of integral electrodes for connection to the hydrophilic-matrix conductor. For example, a device utilizing a substrate with electrodes on the opposite side to the hydrophilic matrix conductor, having holes through the substrate to provide electrical contact between electrodes and the conductor will function equivalently to the embodiment shown in FIGS. 4A-4E.

The device of FIGS. 5A-5E is an example of an integrated-electrokinetic circuit featuring hydrophilic-matrix conductors and integral electrodes. This device is a self-contained micro-analytical system on a chip. In addition to hydrophilic matrix conductors taught in the embodiments of FIGS. 1-3 and an integrated electrokinetic pump taught in the embodiment of FIG. 4, this embodiment teaches additional integrated-electrokinetic circuit elements such as reservoirs, reservoirs containing reagents, conductor junctions, reaction zones and integral probe-electrodes. In this embodiment there is a first hydrophilic-matrix conductor 2, and a second, optional hydrophilic-matrix conductor 2d contacting it and forming a junction with it. Conductors 2 and 2d are in the form of strip-lines. There is a hydrophilic-matrix reservoir 2a contacting conductor 2 at one end and a second reservoir 2b contacting conductor 2 at the other end. Optional hydrophilic-matrix reservoir 2c contacts optional conductor 2d at its end. Reservoirs 2a, 2b and 2c have a large surface area and volume relative to conductors 2 and 2d. The reservoirs can contain dry reagent when fabricated, as determined by the specific application of the micro-analytical system. There are integral electrodes 7a, 7b and 7c providing electrical contact to each of the reservoirs. Electrodes 7 are insulated along their length with insulator 8. Passages through the insulators 8a, 8b and 8c are provided at locations 9a, 9b and 9c that permit electrical contact between electrodes 7a and 7b and 7c and the hydrophilic matrix reservoirs 2a, 2b and 2c. All of the above hydrophilic-matrix circuit components are coated with an insulating but water-permeable cover layer 3. There is an opening 4 through cover layer 3 over conductor 2.

The device of this embodiment also constitutes a micro-electrokinetic pumping system for delivery of fluids through conductor 2. Fluids may be pumped from reagent reservoirs 2a or optional 2c, along conductor 2 to a region 6 of the device where there are separators, analytical cells or reactors as described below, then to a waste reservoir 2b. Reaction zone 6, including a means for monitoring species concentration therein, is a hydrophilic-matrix region along conductor 2 in which chemical reactions, separations and species detections take place. The concentration of chemical species within the reaction zone 6 may be probed by a variety of techniques well known in the art including by optical absorbance, by luminescence or laser induced fluorescence of luminescent or fluorescent molecules or labels in the reaction zone 6 by optical detector 11 (not illustrated) or by electrochemical detection using electrochemical probe electrode(s) 7d. The reaction zone 6 may be the same composition as the hydrophilic matrix conductor 2, as in the electrophoretic separation application of this device described later. In other applications of the micro-analytical system, reaction zone 6 may be a different composition. For example in the ligand-binding assay application of the micro-analytical system reaction zone 6 contains reagents that bind with species being transported along conductor 2.

Referring to the B-B' cross-section of FIG. 5C, in operation a portion of the top surface of the device is immersed in an aqueous medium. Water 50 is transported as vapor through the water vapor-permeable cover layer 3 into the initially dry, inactive hydrophilic-solid matrix conductors 2 and 2d, reservoirs 2a, 2b and 2c, and reaction or separation zone 6. The cover layer 3 is otherwise insulating, that is, it does not transport other solute species, ions or electrons.

Figure 5A:
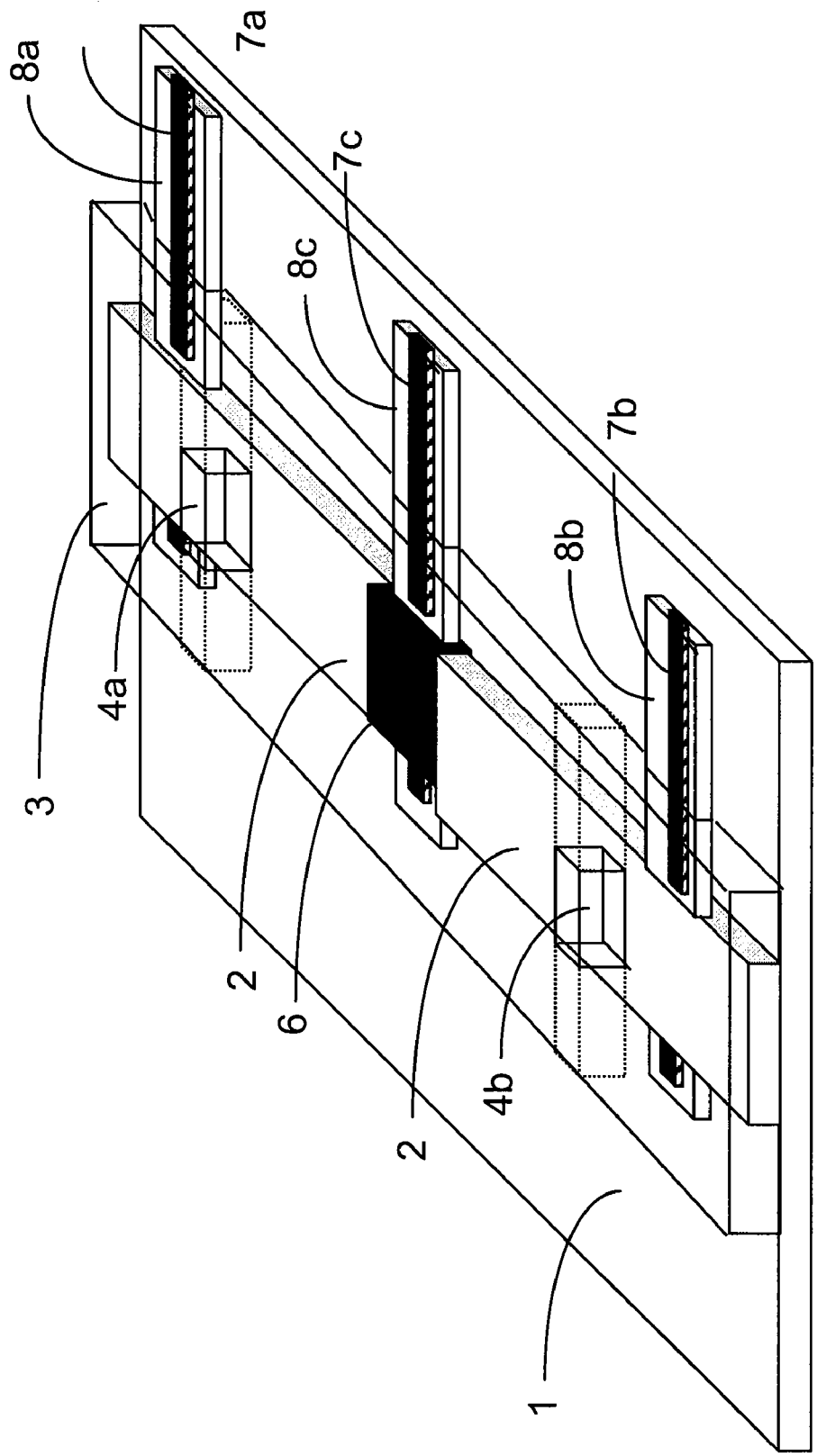
FIG. 5A is a schematic perspective view of an integrated-electrokinetic circuit according to an embodiment of the invention.

One use of the micro-analytical system of FIG. 5 is in a ligand-binding assay. In this application an electrolyte solution containing the target molecule to be assayed is introduced into the hydrophilic-matrix conductor 2 through orifice 4. This is achieved by electrokinetic pumping when a positive voltage is applied to the electrolyte solution by integral electrode 7e relative to the voltage of waste reservoir 2b applied through electrode 7b. Thus, sample solution is pumped through 2 to zone 6 which contains an immobilized receptor or capture module that binds the target molecule. The bound target molecule may be detected within zone 6. A typical detection strategy known in the art is to introduce a label molecule that also binds to the target molecule. The label molecule will traverse the conductor 2 to zone 6 where it binds to the target molecule. The concentration of the bound entity including the bound target molecule and label is detected by assaying the concentration of the label as is known in the art. Labels may include but are not limited to fluorescent, luminescent, optically absorbing or enzymatic labels. In this assay method only the bound label concentration that is related to bound target molecule concentration is measured, because unbound label molecules are removed from the reaction zone 6 by electrokinetic pumping and are not detected. The concentration of chemical species within the reaction layer 6 is measured by optical detector 11 or by integral electrochemical probe electrode 7d. In optical detection methods detectors are usually off-chip devices, although integral optical detection devices are known in the art of ligand-binding devices. Electrochemical detectors are particularly suited to integration as described in this embodiment of the invention. An integral electrochemical probe electrode 7d (or array of electrodes constituting an electrochemical cell) and the associated isolation insulator 8d are shown in FIG. 5A. A passage 9d that connects probe electrode 7d to the reaction zone 6 is shown in FIG. 5B and 5D. Also shown are one or more electrode coatings 10 interposed between the probe electrode and the reaction zone. In this configuration, the electrochemical probe electrode(s) 7d and coatings 10 together constitute a biosensor detector located in a zone of the hydrophilic-matrix conductor.

There are numerous combinations of electrodes 7d and coatings 10 known in the prior art of electrochemical biosensors. Indeed, some biosensors have been used in prior-art separation devices using electrochemical detection.

To illustrate the types of biosensors that might be used in a device of the present invention, consider a reaction zone 6 in which a reaction takes place that produces a change of pH. Electrodes 7d and coating 10 might then be a pH electrode with a pH selective membrane. In another example, the reaction being probed might produce a change in hydrogen peroxide concentration for example if the label molecule is the enzyme glucose oxidase. In this example the electrode 7d is a platinum metal anode and the coating 10 is a hydrogen peroxide selective layer. Those skilled in the art will appreciate that there are many possible biosensor devices that could be used in this invention.

In those cases where the probe reaction is enzyme based, such as in a ligand binding assay using an enzyme probe, it can be advantageous to introduce substrate for the enzyme reaction after the binding reaction has occurred. This can be achieved by electrokinetic pumping of the enzyme substrate contained in reagent reservoir 2c. Reagent flows from 2c via hydrophilic-matrix conductors 2d and 2 through reaction zone 6 to waste reservoir 2b. Pumping is achieved by applying a positive voltage to reagent reservoir 2c through electrode 7c relative to the voltage of waste reservoir 2b. Those skilled in the art of electrochemical detection in electrostatically pumped systems appreciate that there are other arrangements of reaction zone 6 and its electrochemical detectors with respect to the high voltage electrokinetic pumping electrodes. For example when pumping electrode 7b is located just upstream of 6 in conductor 2 electrode 7d is located outside of the high field region, thus simplifying the electrochemical detection process. Such other electrode arrangements are clearly contemplated as variations of the current invention.

Another application of the micro-analytical system of FIG. 5A is in electrostatically pumped separations. In this case, the reaction zone 6 is a separation column. Its contains a matrix suitable for separating species transported through it. In use, a carrier electrolyte is pumped from carrier reservoir 2a to waste reservoir 2b. Pumping is achieved by applying a positive voltage to carrier reservoir 2a through electrode 7a relative to waste reservoir 2b. A segment of sample is electrostatically pumped through port 4 into the carrier electrolyte flowing in conductor 2. This is achieved by switching the positive potential from carrier reservoir 2a applied through electrode 7a to the sample solution applied through electrode 7e contacting it, then back to 7a. Species become spatially separated as they are electrostatically transported along the hydrophilic-matrix in the separation region 6 as powered by electrodes 7a and 7b. Charged species are separated by differential electrical mobility (electrophoresis), uncharged species are separated by differential residence on absorbing surfaces of the separation medium within the hydrophilic matrix (chromatography). The concentration versus time profile of separated chemical species as they traverse the reaction zone 6 is monitored by an optical detector 11 or an integral electrochemical biosensor (electrode 7d with coatings 10). The composition of separation zone 6 could be the same as hydrophilic-matrix conductor 2 in the simplest implementation of the device in an electrophoretic separation. In another implementation in a chromatographic separation, zone 6 may be two components as described in the hydrophilic-matrix conductor of FIG. 3E.

In one specific example of a separation application, the species to be separated are DNA fragments with fluorescent labels, such as might be obtained from a Sanger reaction or a primer extension reaction.

In one method of manufacture of the micro-analytical system of the FIG. 5A embodiment, a single layer of a hydrophilic-matrix material is deposited onto a planar insulating substrate with integral thin film electrodes. The hydrophilic matrix is formed into the pattern of the integrated-electrokinetic circuit consisting of reservoirs and conductors shown in FIG. 5A using photo-processing methods described earlier. Either a single circuit or an array of circuits on a chip can be fabricated with the same photo-process. Reagents are added to photo-formed reservoirs by an impregnation step using a solution that contains reagent applied locally over a reservoir region. The solution is applied by a process of dispensing from a nozzle, spotting or an ink-jet deposition process. Different reservoir contents can be achieved by applying different impregnating solutions over each reservoir. Cover layer 3 is then deposited and formed using processes described earlier.

The micro-analytical system of FIG. 5 is convenient to package because all of the component reservoirs and conductors are electrically isolated from the sample fluid and from one another by the cover layer 3. However, the reservoirs are not vented in this device, they are sealed. In this case there will be an internal pressure build-up within the sealed reservoirs resulting from significant efflux or influx of electrolyte during pumping, such back-pressure impeding further pumping. Thus this design is appropriate when the amount of material pumped into or out of a reservoir is small compared with its volume. Clearly it is also possible to provide vent openings through cover layer 3 over each reservoir 2*a*, 2*b* and 2*c* to connect them to external electrolyte solution reservoirs in applications where the amount of material to be pumped is sufficient to cause build-up of back-pressure in a sealed reservoir system. In such a vented reservoir device packaging is more complex since the electrical isolation of external reservoirs is necessary to operate the various pumping functions as is appreciated by those in the art.

With the invented micro-analytical system using the invented integrated-electrokinetic circuits, it is now possible to perform many different micro-analytical procedures on a chip. Thus, the use of the invented devices is not limited to ligand-binding assays and separations that described in the embodiment of FIG. 5. It is contemplated that different arrangements of integrated-electrokinetic circuit components according to this invention can provide micro-analytical systems to perform numerous analytical functions. Some other integrated-electrokinetic circuits and components according to this invention used in additional analytical applications include but are not limited to: devices with reaction zones incorporating pcr reactions, devices with reaction zones supporting primer extension reactions in general, devices with reaction zones incorporating restriction enzymes; integrated devices combining the above reaction zones with a hydrophilic-matrix separation column to analyze reaction components, FIG. 6 shows another embodiment of the invention. This device is configured as an array of electrokinetic pumps for transport of a sample solution through an array of reaction zones. In this device a hydrophilic-matrix conductor 2 is deposited onto a planar insulating substrate with integral electrodes 7*a* and 7*b*. The hydrophilic matrix is formed as a parallel array of branch elements joining at a common reservoir 2*b*. Conductors and reservoir are coated with a cover layer 3 of a water vapor-permeable insulator. The device has an array of openings 4 for influx of a sample solution into the hydrophilic-matrix conductor 2. There is one opening 4 in each of the conductor branches. A reaction zone 6 is provided at each opening.

In a specific example of the device of FIG. 6 the reaction zones 6 contain immobilized binding molecules. Thus, this embodiment now provides ligand binding arrays and their processes for the manufacture. Such devices are very familiar in the fields of immunoassay and DNA hybridization probes with the added benefit that each element of the binding array can have the sample solution electrostatically pumped to it under device control. In operation, a portion of the top surface of the device is immersed in a sample solution containing one or more species for assay. As in the previous embodiments of this invention, water 50 is transported as its vapor into the hydrophilic matrix. Once wet-up the activated hydrophilic matrix becomes a conducting electrolyte. Electrokinetic transport occurs when a voltage is applied to the electrodes 7*a* and 7*b*. In this embodiment it is preferable that the hydrophilic matrix be chosen with a large electroosmotic coefficient such that electroosmosis of the entire solution is the fastest transport mode. The purpose of the electrokinetic pump is to transport target molecules from the bulk sample solution to the reaction zone containing ligand where they are bound and detected. Electrokinetic transport of sample solution containing target molecules to the binding site enhances the speed and sensitivity of the ligand-binding reaction compared to the standard ligand-binding array where the target molecules diffuse from the bulk solution to the binding site.

Each of the reaction zones 6 of the FIG. 6 embodiment can contain a different binding molecule as is typical of ligand-binding arrays. In a variation of the FIG. 6 embodiment it is also possible to configure a separate electrode for each of the branch elements of the hydrophilic matrix 2. In this way there is additional flexibility to apply different voltages for each branch, or to regulate the timing at which each pump is activated. Those skilled in the art will recognize that there can be different arrangements of the location of pumping electrodes relative to openings 4 and reaction zones 6 that will also achieve the desired object of electrostatically pumping a test solution through the reaction zone. For example the opening could be located over a hydrophilic matrix conductor between the integral pumping electrodes. Also, one of the electrokinetic-pump electrodes could be immersed in, and in contact with the sample solution. Non-integral electrodes immersed in aqueous reservoirs connected to the sample solution and reservoir 2*b* also could provide the electrokinetic pump's power. The detailed position of the ligand-binding elements 6 relative to the orifices 4 and conductor 2 maybe somewhat different from the schematic of FIG. 6. Orifices 4 may be located at an end location of the conduit as in the embodiment of FIG. 1. Instead of locating the ligand-binding elements as coatings over orifices 4 as shown in FIG. 6, the ligand-binding elements may be co-planar with the conductor 2.

In the example shown in FIG. 6 integral electrodes 7*a* and 7*b*, hydrophilic-matrix conductors 2 and water-permeable insulator layers 3 with openings 4 are fabricated on a planar insulator 1, as in the previous embodiments of the invention. The ligand-binding elements may be applied onto openings 4 by dispensing from a nozzle, by ink-jet printing, or by a spotting processes as are known in the art of ligand-binding arrays.

Although the invention has been described above with reference to specific preferred embodiments and examples of the device and method of manufacture of the invention, it will be understood that other specific devices and methods are also encompassed by the present invention which is only defined by the scope of the appended claims.

What is claimed is:

1. A device for electrokinetic transport of an aqueous solute, comprising
an electrically insulating substrate;
a conductor element for electrokinetic transport of the solute, the conductor element being in the form of a solid hydrophilic-matrix layer on the substrate, the matrix layer being in a substantially dry, inactive state wherein electrokinetic transport is substantially prevented;
a pair of spaced apart electrodes in electric contact with the conductor element at spaced apart locations for applying an electric potential across the conductor element; and
a cover layer for electrically insulating and encapsulating the conductor element on the substrate, the cover layer being made of an encapsulating material which is water vapour permeable, but impermeable to the solute;
whereby exposure of the hydrophilic matrix to water converts the matrix from the inactive state to a hydrated, active state permitting electrokinetic transport of the solute.

2. The device of claim 1, further comprising a means for introducing water into the conductor element.

3. The device of claim 2, further comprising a means for introducing the aqueous solute into the conductor element.

4. The device of claim 1, wherein the solid hydrophilic-matrix layer is micro-fabricated onto the substrate.

5. The device of claim 1, wherein the solid hydrophilic-matrix layer is a dry reagent film.

6. The device of claim 1, wherein the cover layer is micro-fabricated onto the conductor element and the substrate.

7. The device of claim 1, wherein at least one of the cover layer and the substrate has at least one portion which is permeable to water vapor.

8. The device of claim 1, wherein the substrate consists of electrically insulating material.

9. The device of claim 1, wherein the substrate includes a layer of electrically conductive material and a layer of electrically insulating material intermediate the layer of conductive material and the conductor element.

10. The device of claim 1, wherein one of the substrate and the cover layer has a pair of openings for input and output of the solute species to be transported through the conductor element.

11. The device of claim 1, comprising at least one region for introducing the solute for one of transport, separation and chemical reaction within the conductor element, and a separate means for introducing water only into the conductor element.

12. A device for electrokinetic transport of an aqueous solute, comprising
an electrically insulating substrate;
a conductor element for electrokinetic transport of the solute, the conductor element being in the form of a solid hydrophilic-matrix layer on the substrate, the matrix layer being in a substantially dry, inactive state wherein electrokinetic transport is substantially prevented and having a first surface engaging the substrate and a second surface;
a cover layer for electrically insulating and covering the second surface, the cover layer being impermeable to the solute; and
a pair of spaced apart electrodes in electric contact with the conductor element at spaced apart locations for applying an electric potential across the conductor element; whereby exposure of the hydrophilic matrix to water converts the matrix from the inactive state to a hydrated, active state permitting electrokinetic transport of the solute and wherein the electrodes are applied to the substrate and the device further includes an insulator layer for electrically insulating each electrode, the insulator layer having an opening in each region of overlap between one of the electrodes and the conductor element for permitting electric contact of the conductor element with the integral electrodes for electrokinetic pumping.

13. A device for electrokinetic transport of an aqueous solute, comprising
an electrically insulating substrate;
a conductor element for electrokinetic transport of the solute, the conductor element being in the form of a solid hydrophilic-matrix layer on the substrate, the matrix layer being in a substantially dry, inactive state wherein electrokinetic transport is substantially prevented and having a first surface engaging the substrate and a second surface;
a cover layer for electrically insulating and covering the second surface, the cover layer being impermeable to the solute; and
a pair of spaced apart electrodes in electric contact with the conductor element at spaced apart locations for applying an electric potential across the conductor element; whereby exposure of the hydrophilic matrix to water converts the matrix from the inactive state to a hydrated, active state permitting electrokinetic transport of the solute and the device further comprising an input region for supply of solute into the conductor element and an output region spaced apart therefrom for removal of transported solute from the conductor element.

14. The device of claim 13, wherein the hydrophilic matrix of the conductor element is water insoluble in the input and output regions.

15. The device of claim 14, wherein the conductor element further comprises a reservoir region intermediate the input and output regions and including at least one chemical reactant for interaction with the transported solute.

16. The device of claim 15, further comprising an electrode for applying an electric potential to the reservoir region.

17. The device of claim 15, wherein the conductor element includes a plurality of the reservoir regions.

* * * * *